(12) United States Patent
Fletcher et al.

(10) Patent No.: US 9,547,803 B2
(45) Date of Patent: Jan. 17, 2017

(54) MODULATION GUIDED PHASE UNWRAPPING

(71) Applicant: CANON KABUSHIKI KAISHA, Tokyo (JP)

(72) Inventors: Peter Alleine Fletcher, Rozelle (AU); Ruimin Pan, Macquarie Park (AU)

(73) Assignee: Canon Kabushiki Kaisha, Tokyo (JP)

( * ) Notice: Subject to any disclaimer, the term of this patent is extended or adjusted under 35 U.S.C. 154(b) by 46 days.

(21) Appl. No.: 14/576,974

(22) Filed: Dec. 19, 2014

(65) Prior Publication Data
US 2015/0178905 A1    Jun. 25, 2015

(30) Foreign Application Priority Data

Dec. 23, 2013    (AU) .................................. 2013273822

(51) Int. Cl.
| | |
|---|---|
| G06K 9/00 | (2006.01) |
| G06K 9/46 | (2006.01) |
| A61B 6/00 | (2006.01) |
| G06T 7/00 | (2006.01) |
| G03H 5/00 | (2006.01) |

(52) U.S. Cl.
CPC ............. *G06K 9/4604* (2013.01); *A61B 6/484* (2013.01); *A61B 6/52* (2013.01); *G06T 7/0085* (2013.01); *G06T 7/0095* (2013.01); *G06T 2207/10116* (2013.01)

(58) Field of Classification Search
CPC ................ G06K 9/00; G06T 7/00; A61B 6/00
USPC ............................ 382/128–134, 211; 378/36
See application file for complete search history.

(56) References Cited

U.S. PATENT DOCUMENTS

| | | | | |
|---|---|---|---|---|
| 6,571,014 | B1* | 5/2003 | Larkin ................... | G06T 9/001 |
| | | | | 382/125 |
| 8,886,283 | B1* | 11/2014 | Chen ............................ | 382/128 |
| 2002/0076104 | A1* | 6/2002 | Sun ........................ | G01B 11/25 |
| | | | | 382/173 |

FOREIGN PATENT DOCUMENTS

WO    2010/050611 A1    5/2010

OTHER PUBLICATIONS

Gai et al., "Fringe image analysis based on the amplitude modulation method", Optics Express, vol. 18, Issue 10, pp. 10704-10719 (2010).

(Continued)

*Primary Examiner* — Abolfazl Tabatabai
(74) *Attorney, Agent, or Firm* — Canon USA, Inc. I.P. Division

(57) ABSTRACT

A method for determining a phase for a captured image, the method comprising forming a demodulated image defining wrapped phase values and modulation values, each being associated with at least one region in the captured image; identifying a position of an edge in the captured image dependent upon the modulation values; determining a position of substantial change in the wrapped phase values in the captured image dependent upon the identified position of the edge, and determining at least one unwrapped phase value based on the position of the edge and the position of the substantial change in the wrapped phase values by shifting a position of the substantial change in the wrapped phase values to the identified position of the edge, so that said unwrapped phase value is adjusted by at least one cycle.

12 Claims, 25 Drawing Sheets

(56) References Cited

OTHER PUBLICATIONS

European Patent Application No. 14199231.3-1906, Invitation pursuant to Article 94(3) and Rule 71 (1) EPC, dated Apr. 25, 2016.

* cited by examiner

MODULATION GUIDED PHASE UNWRAPPING

REFERENCE TO RELATED PATENT APPLICATION

This application claims the benefit under 35 U.S.C. §119 of the filing date of Australian Patent Application No. 2013273822, filed 23 Dec. 2013, hereby incorporated by reference in its entirety as if fully set forth herein.

TECHNICAL FIELD

The current invention relates X-ray imaging, and in particular, to the extraction of underlying phase information from a set of images obtained in an X-ray Talbot interferometry system.

BACKGROUND

In the last century or so a large number of techniques have been developed to make (normally invisible) phase variations visible in imaging devices. These techniques include Zernike phase contrast, Nomarski differential interference contrast, generalized phase contrast, Foucault knife edge, shadowgraph and dark-field.

More recently there has been progress in extending some of these techniques to X-ray imaging. Phase-contrast X-ray imaging offers the ability to image soft tissues, where conventional absorption X-ray imaging does not produce a detectible contrast due to low absorption in soft tissues. A number of new phase-contrast techniques have been developed to address the particularly difficult nature of X-rays. These difficulties relate primarily to the difficulty of focusing and imaging X-ray beams, due to both their penetrating power and the small range of refractive indices available. Current techniques include TIE (Transport of Intensity Equation), phase contrast imaging and ptychography. Another current technique is known as "X-ray Talbot interferometry" (XTI), which yields intermediate images that encode one or more differential phase images. The XTI method when implemented using simple linear gratings gives one differential phase image. XTI implemented with two dimensional (crossed) gratings yields an x differential phase image and a y differential phase image. The differential phase in x and y directions will be referred to as 'phase' hereafter in this disclosure for simplicity.

A problem with phase imaging is that the recovered phase information is almost always 'wrapped' because it is embedded in a sinusoidal function. In other words, the phase value recovered from the phase imaging system in question is the underlying phase value modulo $2\pi$ radians. A typical phase unwrapping method looks for discontinuities in the phase and compensates for sudden jumps or drops by adding or subtracting integer multiples of $2\pi$ to restore the true phase values.

Phase unwrapping is in general a difficult problem because the problem is inherently ambiguous and there is no consistent way to distinguish between discontinuities caused by wrapping, and discontinuities which exist in the true, unwrapped, phase. A phase discontinuity is associated with a "residue", which is a single point of discontinuity in the phase that constitutes the start or end-point of an extended region of discontinuity.

To unwrap the phase, some methods operate in three steps, namely finding residues, joining residues together to minimize some measure of discontinuity, and then using a flood-fill algorithm to correct the phase values in regions.

However, because these algorithms are region-based, when they fail they can produce extremely visible artifacts, such as an offset of $2\pi$ which covers a substantial fraction of the area of an image.

FIG. 3 illustrates an example of prior art incorrect phase unwrapping results. FIG. 3 is a hypothetical one-dimensional example of a genuine phase edge treated as a phase wrapping effect by a prior art phase unwrapping algorithm. FIG. 3 depicts a real discontinuity in a phase signal, depicted in (310), in which a signal 311 gradually drops to a minimum value 312 and then jumps to a much higher value 313 before it slowly decreases again as depicted at 314. One current phase unwrapping method will detect this discontinuity and shift the region 314 on the right of the discontinuity 312/313 downward by $2\pi$ based on the fact that slopes of the signal just before (see 316) and after (see 315) the discontinuity point 312/133 seem to match. However, the result depicted at 320 not only mistakenly removes a real phase edge, but it also offsets the phase value by $2\pi$, an error that will propagates to the end of the signal.

SUMMARY

It is an object of the present invention to substantially overcome, or at least ameliorate, one or more disadvantages of existing arrangements.

Disclosed are arrangements, referred to as Modulation Guided Phase Unwrapping (MGPU) arrangements, which seek to address the above problems by refining the position of a detected discontinuity in a phase values from a captured image dependent upon a detected local minimum in a modulation value for the captured image.

According to a first aspect of the present invention, there is provided a method for determining a phase for a captured image, the method comprising the steps of:

forming a demodulated image from the captured image, said demodulated image defining a plurality of wrapped phase values and a plurality of modulation values, each wrapped phase value and each modulation value being associated with at least one region in the captured image;

identifying a position of an edge in the captured image dependent upon the plurality of modulation values;

determining a position of substantial change in the wrapped phase values in the captured image dependent upon the identified position of the edge, and;

determining at least one unwrapped phase value based on the position of the edge and the position of the substantial change in the wrapped phase values by shifting a position of the substantial change in the wrapped phase values to the identified position of the edge, so that said unwrapped phase value is adjusted by at least one cycle.

According to another first aspect of the present invention, there is provided an apparatus for determining a phase for a captured image, the apparatus comprising:

a processor; and a memory storing a computer executable program for directing the processor to perform a method comprising the steps of:

forming a demodulated image from the captured image, said demodulated image defining a plurality of wrapped phase values and a plurality of modulation values, each wrapped phase value and each modulation value being associated with at least one region in the captured image;

identifying a position of an edge in the captured image dependent upon the plurality of modulation values;

determining a position of substantial change in the wrapped phase values in the captured image dependent upon the identified position of the edge, and;

determining at least one unwrapped phase value based on the position of the edge and the position of the substantial change in the wrapped phase values by shifting a position of the substantial change in the wrapped phase values to the identified position of the edge, so that said unwrapped phase value is adjusted by at least one cycle.

According to another first aspect of the present invention, there is provided a non-transitory computer readable storage medium storing a computer executable program for directing a processor to perform a method for determining a phase for a captured image, the method comprising the steps of:

forming a demodulated image from the captured image, said demodulated image defining a plurality of wrapped phase values and a plurality of modulation values, each wrapped phase value and each modulation value being associated with at least one region in the captured image;

identifying a position of an edge in the captured image dependent upon the plurality of modulation values;

determining a position of substantial change in the wrapped phase values in the captured image dependent upon the identified position of the edge, and;

determining at least one unwrapped phase value based on the position of the edge and the position of the substantial change in the wrapped phase values by shifting a position of the substantial change in the wrapped phase values to the identified position of the edge, so that said unwrapped phase value is adjusted by at least one cycle.

According to another first aspect of the present invention, there is provided a n unwrapped phase record determined from wrapped phase values and a plurality of modulation values from a captured image, the unwrapped phase record being determined using a method comprising the steps of:

forming a demodulated image from the captured image, said demodulated image defining the plurality of wrapped phase values and the plurality of modulation values, each wrapped phase value and each modulation value being associated with at least one region in the captured image;

identifying a position of an edge in the captured image dependent upon the plurality of modulation values;

determining a position of substantial change in the wrapped phase values in the captured image dependent upon the identified position of the edge, and;

determining at least one unwrapped phase value in the unwrapped phase record based on the position of the edge and the position of the substantial change in the wrapped phase values by shifting a position of the substantial change in the wrapped phase values to the identified position of the edge, so that said unwrapped phase value is adjusted by at least one cycle.

Other aspects of the invention are also disclosed.

BRIEF DESCRIPTION OF THE DRAWINGS

One or more embodiments of the invention will now be described with reference to the following drawings, in which.

DETAILED DESCRIPTION INCLUDING BEST MODE

Context

Figure 1:
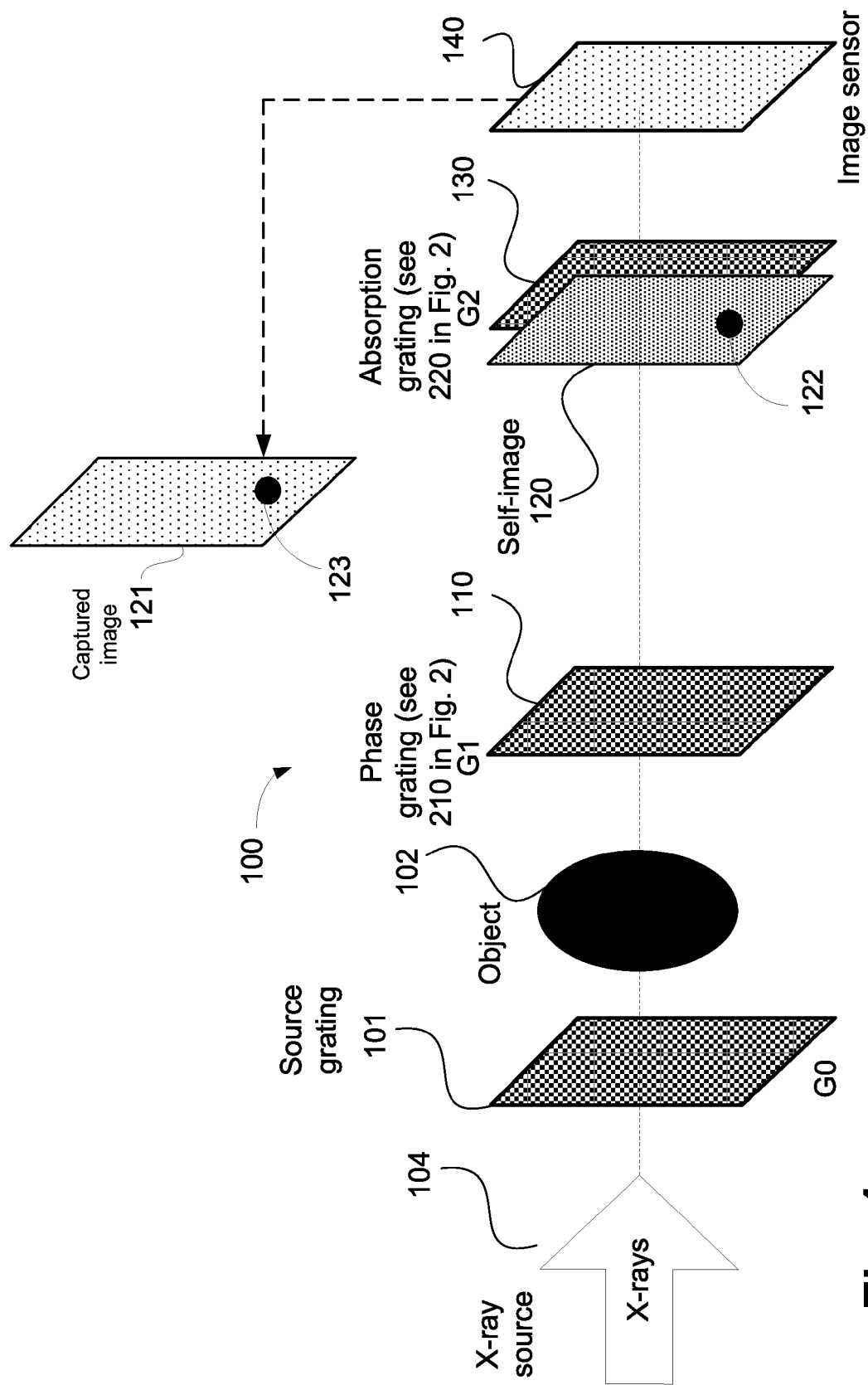
FIG. 1 is a diagram of an experimental set-up for an X-ray Talbot interferometer according to one MGPU arrangement.

Where reference is made in any one or more of the accompanying drawings to steps and/or features, which have the same reference numerals, those steps and/or features have for the purposes of this description the same function (s) or operation(s), unless the contrary intention appears.

It is to be noted that the discussions contained in the "Background" section and that above relating to prior art arrangements relate to discussions of documents or devices which may form public knowledge through their respective publication and/or use. Such discussions should not be interpreted as a representation by the present inventor(s) or the patent applicant that such documents or devices in any way form part of the common general knowledge in the art.

FIG. 1 is a diagram of an experimental set-up 100 for an X-ray Talbot interferometer (XTI) according to one MGPU arrangement. FIG. 1 shows an example of an XTI. A source grating G0 (ie 101), an object 102 and a phase grating G1 (ie 110) are illuminated by an X-ray source 104. A self-image 120, referred to as an interferogram, is formed behind the phase grating G1 (ie 110) due to the Talbot effect. The term "Interferogram" is a general term for any fringe image generated using imaging techniques where phase differences are used to form images. Since the phase of the X-ray wave is shifted by the object 102, the self-image 120 is deformed with respect to the object 102. By analysing the deformed self-image 120, the characteristics of the object 102 can be deduced. Because this type of X-ray imaging uses phase differences instead of absorption to produce contrast, the resolution of the XTI system is much higher than that achieved using a conventional absorption X-ray approach. In FIG. 1, an absorption grating G2 (ie 130) at the position of the self-image 120 helps generate a moiré image (fringe image) which constitutes the self-image 120. Normally the period of the absorption grating G2 (ie 130) is designed to be similar to that of the self-image 120, so that the moiré image generated by superposing the deformed self-image 120 and the absorption grating G2 (ie 130) produces, as described hereinafter in more detail with reference to FIGS. 20A-20C, a much larger version of the original self-image 120 at the image sensor 140 which resolves the image to produce a captured XTI image 121, which is is one type of interferogram.

Figure 20A:
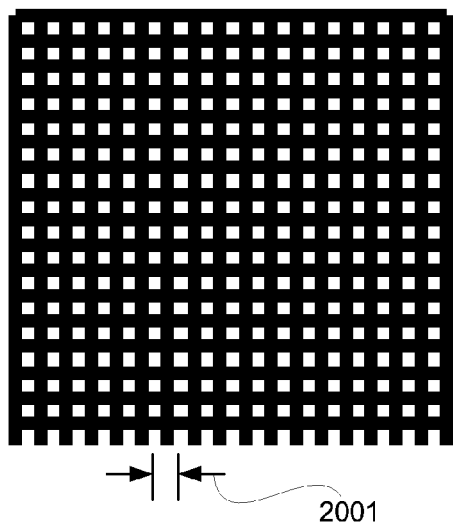
FIGS. 20A-20C illustrate how the moiré effect can be used to produce a larger version of the original image.
Figure 20B:
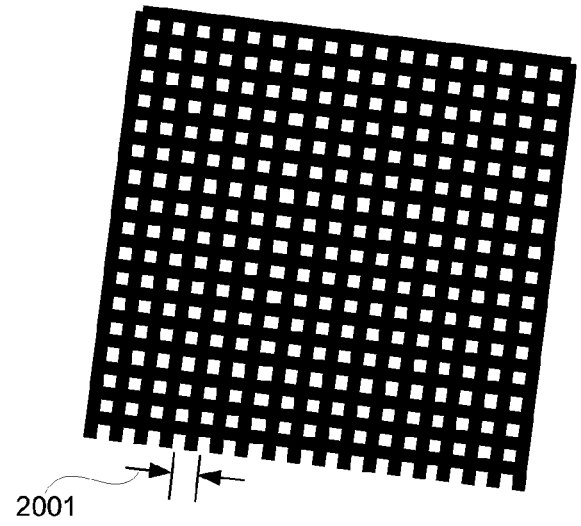
Figure 20C:
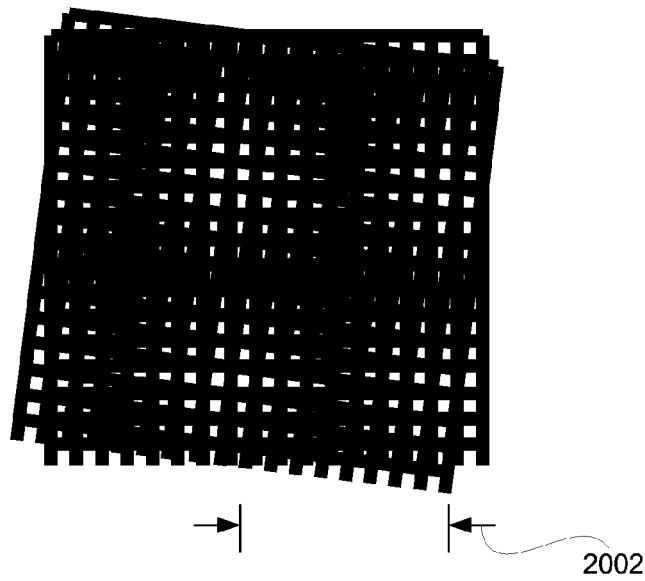

FIGS. 20A-20C illustrate how the moiré effect produces a larger version of the original image. FIG. 20A shows a fringe image having a fringe period 2001 and FIG. 20B shows a slightly tilted version of FIG. 20A, having the same fringe period 2001. When these two fringe images are superimposed as depicted in FIG. 20C and low-pass filtered at the sensor, a moiré image with larger fringe period depicted by 2002 is formed. Due to limited sensor resolution, fringe images such as the ones in FIG. 20A or 20B are difficult or impossible for some image sensors to resolve. The moiré effect, however, makes it possible for some low-cost image sensors to resolve fringe images with smaller fringe periods.

Figure 22:
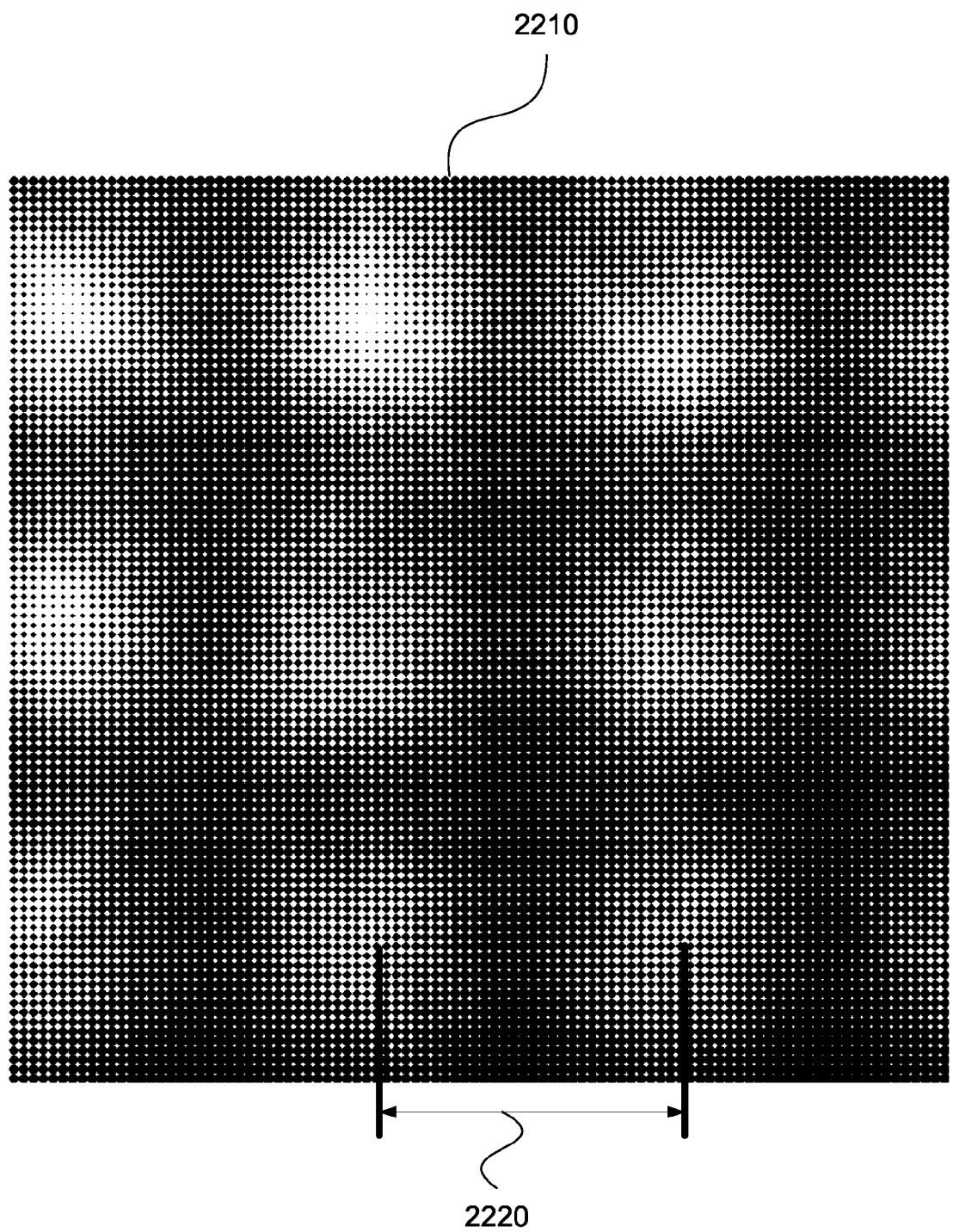
FIG. 22 shows an example of a 96×96 region of an XTI moiré image with a fringe period of 32 pixels.

FIG. 22 shows an example 2210 of a real moiré image from an XTI system. The image is of a 96×96 region from a moiré image, with a 32-pixel period in the moiré fringe. The underlying object in this region is part of an animal with fur, thus the moiré image is distorted everywhere. This image is only one of 16, with each image containing different phase steps, from which an amplitude and phase image can be demodulated. A reference numeral 2220 in FIG. 22 indicates the fringe period of the XTI captured images, which is 32 pixels per fringe. The term 'fringe period' is defined as the number of pixels between two intensity value peaks of the fringe in an x or a y direction (ie 2220). In this MGPU arrangement, the fringe periods in x and y directions are assumed to be the same, therefore a single fringe period is used to characterise the fringe image. For example, a fringe period can be 32 pixels per fringe or 8 pixels per fringe, with the former case having a larger fringe period than the latter.

Figure 2:
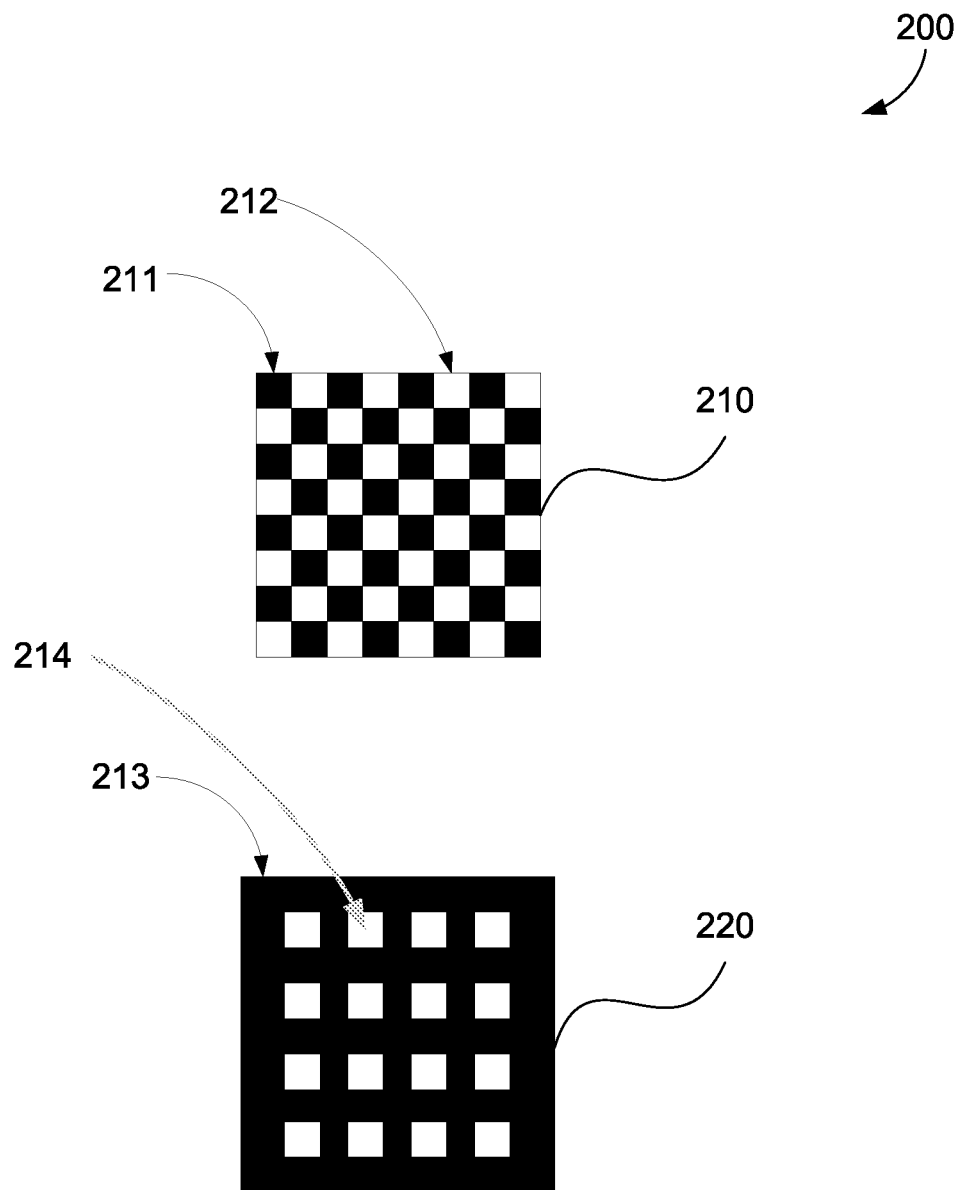
FIG. 2 illustrates an example of the gratings used in the arrangement in FIG. 1.
Figure 3:
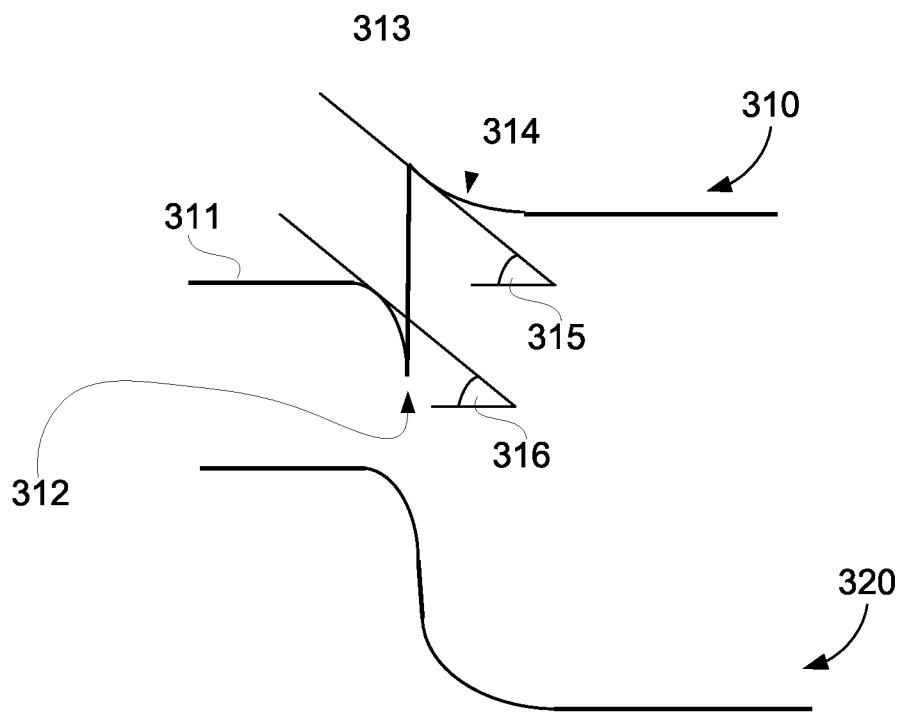
FIG. 3 illustrates an example of prior art incorrect phase unwrapping results.

FIG. 2 illustrates examples of the gratings used in the MGPU arrangement in FIG. 1. A grating 210 is an example of a phase grating that can be used for G1 (ie 110) and a grating 220 is an example of an absorption grating that can be used for G2 (ie 130). In the grating 210, dark areas such as 211 represent regions on the grating G1 (ie 110) where a phase shift of $\pi$ is imposed. Bright areas such as 212 represent regions on the grating G1 (110) where no phase shift is imposed. In the grating 220, dark areas such as 213 represent regions on the grating G2 (ie 130) that absorb most of the incident X-ray energy, whereas bright areas such as 214 represent regions on the grating G2 (ie 130) that let the X-ray energy go through.

The moiré image generated in the XTI system can be approximately expressed as follows:

$$z(r) = \tfrac{1}{4}\alpha(r)(1+m_x(r)\cos(\phi_x(r)))(1+m_y(r)\cos(\phi_y(r))) \quad (1)$$

where $z(r)$ is an intensity value at a position r (depicted as a region 122 in the self image 120 and as a corresponding region 123 in the captured XTI image 121); $m_x(r)$ and $m_y(r)$ are x and y modulation strengths of cosine components; $\phi_x(r)$ and $\phi_y(r)$ are phase functions related to the phases of the object 102 in the x and the y direction namely $\xi_x(r)$, $\xi_y(r)$; and $a(r)$ is the absorption factor that is proportional to the amount of X-ray energy captured in the moiré image. Phase functions in Equation (1), including $\phi_x(r)$, $\phi_y(r)$, $\xi_x(r)$ and $\xi_y(r)$, are in radians.

Accordingly, $z(r)$ is a captured XTI image (also referred to as the moiré image or the fringe image) in which amplitude information relating to the object 102 is contained in amplitude modulation coefficients $m_x(r)$ and $m_y(r)$, and phase information about the object 102 is contained in frequency modulation coefficients $\phi_x(r)$ and $\phi_y(r)$, which in turn are related to phases of the object 102 in the x and the y direction: $\xi_x(r)$, $\xi_y(r)$.

Equation (1) models the image forming process in the XTI system. The object phase $\xi_x(r)$ modulates the phase grating G1 (ie. 110) to produce the frequency modulation coefficient $\phi_x(r)$. The object phase $\xi_y(r)$ modulates the phase grating G1 (ie. 110) to produce the frequency modulation coefficient $\phi_y(r)$. Together with some absorption of the X-ray energy and the amplitude modulation in x and y directions $m_x(r)$ and $m_y(r)$, the XTI system produces a fringe image that is modulated by information from the object (ie. 102).

In order to recover the original information from the object (ie. 102), moiré images $z(r)$ captured in the XTI system 100 need to be demodulated to recover the x and y phases $\xi_x(r)$ and $\xi_y(r)$ of the object 102. In one MGPU example the output, referred to as a demodulated image, of a demodulation process 420 described hereinafter in more detail with reference to FIG. 4 includes five image components namely $a(r)$, $m_x(r)$, $m_y(r)$, $\xi_x(r)$ and $\xi_y(r)$, where $\xi_x(r)$ and $\xi_y(r)$ are derived from $\phi_x(r)$ and $\phi_y(r)$ respectively. The values of the x and y amplitude modulation coefficients, namely $m_x(r)$ and $m_y(r)$, range between 0 and 1 and the values of the demodulated x and y object phase $\xi_x(r)$ and $\xi_y(r)$ range between 0 and $2\pi$. Note that because of the wrapping effect of the cosine function, phase unwrapping is needed to recover the original x and y object phases from their estimation $\xi_x(r)$ and $\xi_y(r)$. That is, phase unwrapping is necessary to find out the underlying x object phase that is $\xi_x(r)+2n\pi$ where n is an unknown integer and the underlying x object phase that is $\xi_y(r)+2m\pi$ where m is an unknown integer. It is convenient to combine the corresponding x and y modulation images ($m_x(r)$ and $m_y(r)$) and phase image ($\xi_x(r)$ and $\xi_y(r)$) to form a complex image with modulation image as the modulus and phase image as the angle. For example, $m_x(r)$ and $\xi_x(r)$ can be expressed as one complex image $c_x(r) = m_x(r)e^{i\xi_x(r)}$. Similarly $m_y(r)$ and $\xi_y(r)$ can be expressed as one complex image $c_y(r) = m_y(r)e^{i\xi_y(r)}$. As described hereinafter in more detail, $c_x(r)$ and $c_y(r)$ are referred to as a combined x image and a combined y image, respectively.

In XTI systems, the phase image represents the derivative of the optical path length (OPL) across the image in a particular direction, e.g. in directions parallel to the x or y axes. The optical path length is the integral of the refractive index along the path of the X-rays, and its derivative will change appreciably where there is some kind of refractive index boundary in the object being imaged. For example, if the object being imaged is a body part, there will be a substantial change in the OPL in the image where there is a transition from air to skin, or between muscle and fat, or between tendon and bone. This change in OPL will result in a large change in the phase value, and it is at these "edge" positions that phase wrapping will occur.

The present disclosure relates to extracting phase information from at least one interferogram image (ie, 121) obtained from an X-ray Talbot interferometry system. Generally, the interferogram images captured in the XTI system are demodulated before the phase information is extracted.

Figure 18A:
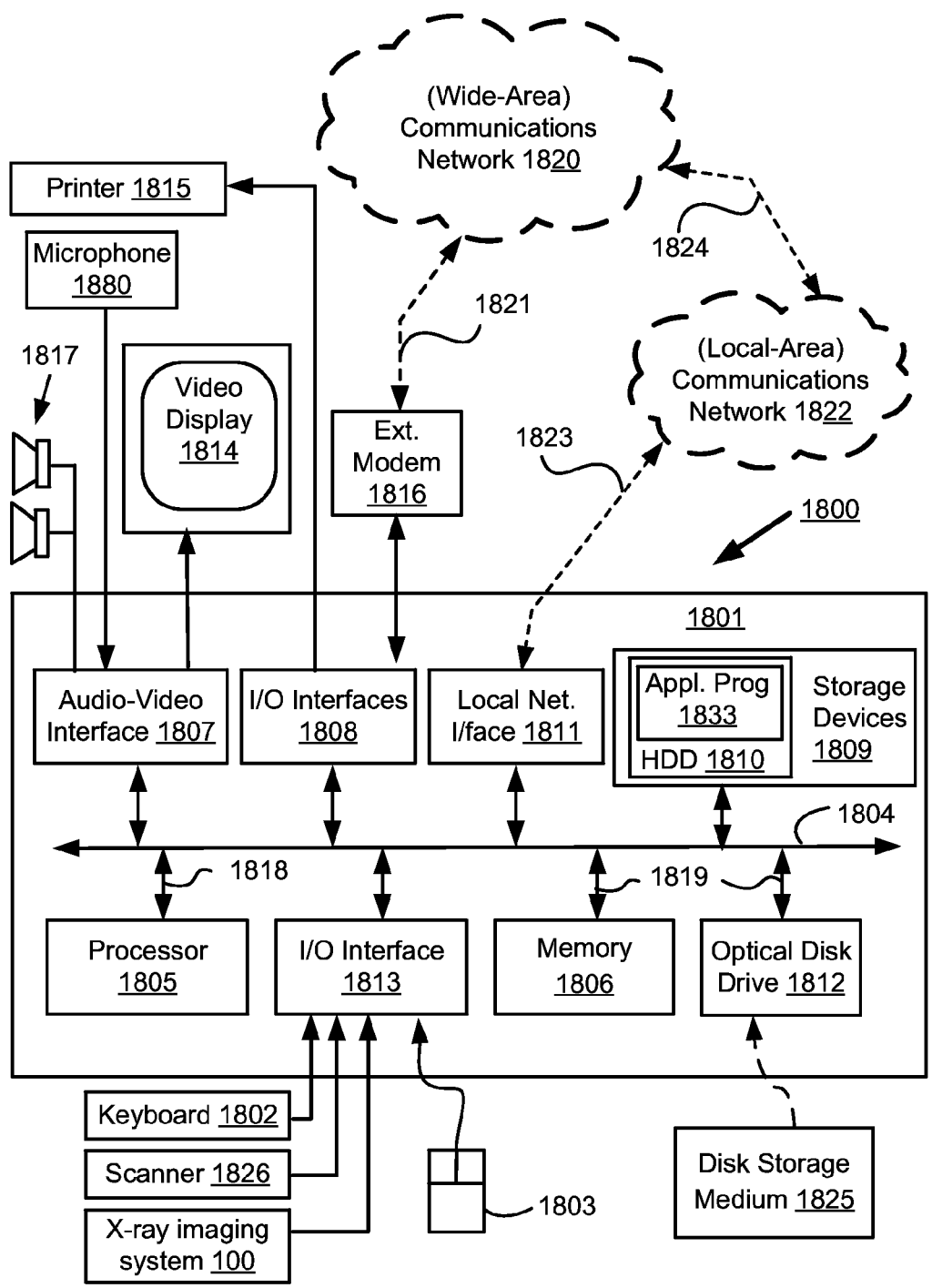
FIGS. 18A and 18B form a schematic block diagram of a general purpose computer system upon which arrangements described can be practiced.
Figure 18B:
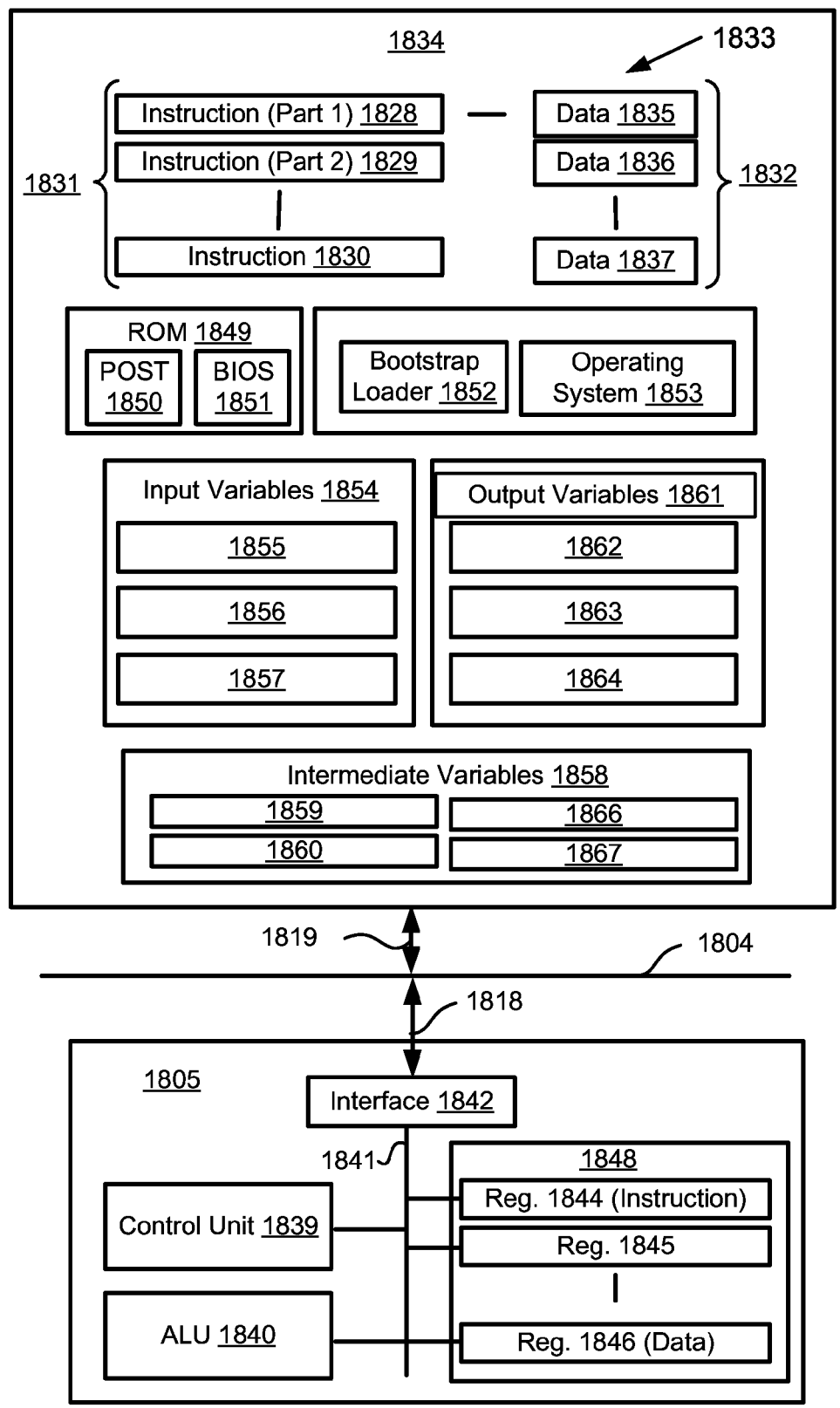

FIGS. 18A and 18B depict a general-purpose computer system 1800, upon which the various MGPU arrangements described can be practiced.

As seen in FIG. 18A, the computer system 1800 includes: a computer module 1801; input devices such as a keyboard 1802, a mouse pointer device 1803, a scanner 1826, an XTI imaging system 100, and a microphone 1880; and output devices including a printer 1815, a display device 1814 and loudspeakers 1817. An external Modulator-Demodulator (Modem) transceiver device 1816 may be used by the computer module 1801 for communicating to and from a communications network 1820 via a connection 1821. The communications network 1820 may be a wide-area network (WAN), such as the Internet, a cellular telecommunications network, or a private WAN. Where the connection 1821 is a telephone line, the modem 1816 may be a traditional "dial-up" modem. Alternatively, where the connection 1821 is a high capacity (e.g., cable) connection, the modem 1816 may be a broadband modem. A wireless modem may also be used for wireless connection to the communications network 1820.

The computer module 1801 typically includes at least one processor unit 1805, and a memory unit 1806. For example, the memory unit 1806 may have semiconductor random access memory (RAM) and semiconductor read only memory (ROM). The computer module 1801 also includes an number of input/output (I/O) interfaces including: an audio-video interface 1807 that couples to the video display 1814, loudspeakers 1817 and microphone 1880; an I/O interface 1813 that couples to the keyboard 1802, mouse 1803, scanner 1826, XTI imaging system 100 and optionally a joystick or other human interface device (not illustrated); and an interface 1808 for the external modem 1816 and printer 1815. In some implementations, the modem 1816 may be incorporated within the computer module 1801, for example within the interface 1808. The computer module 1801 also has a local network interface 1811, which permits coupling of the computer system 1800 via a connection 1823 to a local-area communications network 1822, known as a Local Area Network (LAN). As illustrated in FIG. 18A, the local communications network 1822 may also couple to the wide network 1820 via a connection 1824, which would typically include a so-called "firewall" device or device of similar functionality. The local network interface 1811 may comprise an Ethernet circuit card, a Bluetooth® wireless arrangement or an IEEE 802.11 wireless arrangement; however, numerous other types of interfaces may be practiced for the interface 1811.

The I/O interfaces 1808 and 1813 may afford either or both of serial and parallel connectivity, the former typically being implemented according to the Universal Serial Bus (USB) standards and having corresponding USB connectors (not illustrated). Storage devices 1809 are provided and typically include a hard disk drive (HDD) 1810. Other storage devices such as a floppy disk drive and a magnetic tape drive (not illustrated) may also be used. An optical disk drive 1812 is typically provided to act as a non-volatile source of data. Portable memory devices, such optical disks (e.g., CD-ROM, DVD, Blu-ray Disc™), USB-RAM, portable, external hard drives, and floppy disks, for example, may be used as appropriate sources of data to the system 1800.

The components 1805 to 1813 of the computer module 1801 typically communicate via an interconnected bus 1804 and in a manner that results in a conventional mode of operation of the computer system 1800 known to those in the relevant art. For example, the processor 1805 is coupled to the system bus 1804 using a connection 1818. Likewise, the memory 1806 and optical disk drive 1812 are coupled to the system bus 1804 by connections 1819. Examples of computers on which the described arrangements can be practised include IBM-PC's and compatibles, Sun Sparcstations, Apple Mac™ or a like computer systems.

The MGPU method may be implemented using the computer system 1800 wherein the processes of FIGS. 4-12 to be described, may be implemented as one or more MGPU software application programs 1833 executable within the computer system 1800. In particular, the steps of the MGPU method are effected by instructions 1831 (see FIG. 18B) in the software 1833 that are carried out within the computer system 1800. The software instructions 1831 may be formed as one or more code modules, each for performing one or more particular tasks. The software may also be divided into two separate parts, in which a first part and the corresponding code modules performs the MGPU methods and a second part and the corresponding code modules manage a user interface between the first part and the user.

The MGPU software may be stored in a computer readable medium, including the storage devices described below, for example. The software is loaded into the computer system 1800 from the computer readable medium, and then executed by the computer system 1800. A computer readable medium having such software or computer program recorded on the computer readable medium is a computer program product. The use of the computer program product in the computer system 1800 preferably effects an advantageous apparatus for performing the MGPU methods.

The software 1833 is typically stored in the HDD 1810 or the memory 1806. The software is loaded into the computer system 1800 from a computer readable medium, and executed by the computer system 1800. Thus, for example, the software 1833 may be stored on an optically readable disk storage medium (e.g., CD-ROM) 1825 that is read by the optical disk drive 1812. A computer readable medium having such software or computer program recorded on it is a computer program product. The use of the computer program product in the computer system 1800 preferably effects a MGPU apparatus.

In some instances, the application programs 1833 may be supplied to the user encoded on one or more CD-ROMs 1825 and read via the corresponding drive 1812, or alternatively may be read by the user from the networks 1820 or 1822. Still further, the software can also be loaded into the computer system 1800 from other computer readable media. Computer readable storage media refers to any non-transitory tangible storage medium that provides recorded instructions and/or data to the computer system 1800 for execution and/or processing. Examples of such storage media include floppy disks, magnetic tape, CD-ROM, DVD, Blu-Ray™ Disc, a hard disk drive, a ROM or integrated circuit, USB memory, a magneto-optical disk, or a computer readable card such as a PCMCIA card and the like, whether or not such devices are internal or external of the computer module 1801. Examples of transitory or non-tangible computer readable transmission media that may also participate in the provision of software, application programs, instructions and/or data to the computer module 1801 include radio or infra-red transmission channels as well as a network connection to another computer or networked device, and the Internet or Intranets including e-mail transmissions and information recorded on Websites and the like.

The second part of the application programs 1833 and the corresponding code modules mentioned above may be executed to implement one or more graphical user interfaces (GUIs) to be rendered or otherwise represented upon the display 1814. Through manipulation of typically the keyboard 1802 and the mouse 1803, a user of the computer system 1800 and the application may manipulate the interface in a functionally adaptable manner to provide controlling commands and/or input to the applications associated with the GUI(s). Other forms of functionally adaptable user interfaces may also be implemented, such as an audio interface utilizing speech prompts output via the loudspeakers 1817 and user voice commands input via the microphone 1880.

FIG. 18B is a detailed schematic block diagram of the processor 1805 and a "memory" 1834. The memory 1834 represents a logical aggregation of all the memory modules (including the HDD 1809 and semiconductor memory 1806) that can be accessed by the computer module 1801 in FIG. 18A.

When the computer module 1801 is initially powered up, a power-on self-test (POST) program 1850 executes. The POST program 1850 is typically stored in a ROM 1849 of the semiconductor memory 1806 of FIG. 18A. A hardware device such as the ROM 1849 storing software is sometimes referred to as firmware. The POST program 1850 examines hardware within the computer module 1801 to ensure proper functioning and typically checks the processor 1805, the memory 1834 (1809, 1806), and a basic input-output systems software (BIOS) module 1851, also typically stored in the ROM 1849, for correct operation. Once the POST program 1850 has run successfully, the BIOS 1851 activates the hard disk drive 1810 of FIG. 18A. Activation of the hard disk drive 1810 causes a bootstrap loader program 1852 that is resident on the hard disk drive 1810 to execute via the processor 1805. This loads an operating system 1853 into the RAM memory 1806, upon which the operating system 1853 commences operation. The operating system 1853 is a system level application, executable by the processor 1805, to fulfil various high level functions, including processor management, memory management, device management, storage management, software application interface, and generic user interface.

The operating system 1853 manages the memory 1834 (1809, 1806) to ensure that each process or application running on the computer module 1801 has sufficient memory in which to execute without colliding with memory allocated to another process. Furthermore, the different types of memory available in the system 1800 of FIG. 18A must be used properly so that each process can run effectively. Accordingly, the aggregated memory 1834 is not intended to illustrate how particular segments of memory are allocated (unless otherwise stated), but rather to provide a general view of the memory accessible by the computer system 1800 and how such is used.

As shown in FIG. 18B, the processor 1805 includes a number of functional modules including a control unit 1839, an arithmetic logic unit (ALU) 1840, and a local or internal memory 1848, sometimes called a cache memory. The cache memory 1848 typically includes a number of storage registers 1844-1846 in a register section. One or more internal busses 1841 functionally interconnect these functional modules. The processor 1805 typically also has one or more interfaces 1842 for communicating with external devices via the system bus 1804, using a connection 1818. The memory 1834 is coupled to the bus 1804 using a connection 1819.

The application program 1833 includes a sequence of instructions 1831 that may include conditional branch and loop instructions. The program 1833 may also include data 1832 which is used in execution of the program 1833. The instructions 1831 and the data 1832 are stored in memory locations 1828, 1829, 1830 and 1835, 1836, 1837, respectively. Depending upon the relative size of the instructions 1831 and the memory locations 1828-1830, a particular instruction may be stored in a single memory location as depicted by the instruction shown in the memory location 1830. Alternately, an instruction may be segmented into a number of parts each of which is stored in a separate memory location, as depicted by the instruction segments shown in the memory locations 1828 and 1829.

In general, the processor 1805 is given a set of instructions which are executed therein. The processor 1105 waits for a subsequent input, to which the processor 1805 reacts to by executing another set of instructions. Each input may be provided from one or more of a number of sources, including data generated by one or more of the input devices 1802, 1803, data received from an external source across one of the networks 1820, 1802, data retrieved from one of the storage devices 1806, 1809 or data retrieved from a storage medium 1825 inserted into the corresponding reader 1812, all depicted in FIG. 18A. The execution of a set of the instructions may in some cases result in output of data. Execution may also involve storing data or variables to the memory 1834.

The disclosed MGPU arrangements use input variables 1854, which are stored in the memory 1834 in corresponding memory locations 1855, 1856, 1857. The MGPU arrangements produce output variables 1861, which are stored in the memory 1834 in corresponding memory locations 1862, 1863, 1864. Intermediate variables 1858 may be stored in memory locations 1859, 1860, 1866 and 1867.

Referring to the processor 1805 of FIG. 18B, the registers 1844, 1845, 1846, the arithmetic logic unit (ALU) 1840, and the control unit 1839 work together to perform sequences of micro-operations needed to perform "fetch, decode, and execute" cycles for every instruction in the instruction set making up the program 1833. Each fetch, decode, and execute cycle comprises:

a fetch operation, which fetches or reads an instruction 1831 from a memory location 1828, 1829, 1830;

a decode operation in which the control unit 1839 determines which instruction has been fetched; and an execute operation in which the control unit 1839 and/or the ALU 1840 execute the instruction.

Thereafter, a further fetch, decode, and execute cycle for the next instruction may be executed. Similarly, a store cycle may be performed by which the control unit 1839 stores or writes a value to a memory location 1832.

Each step or sub-process in the processes of FIGS. 4-12 is associated with one or more segments of the program 1833 and is performed by the register section 1844, 1845, 1847, the ALU 1840, and the control unit 1839 in the processor 1805 working together to perform the fetch, decode, and execute cycles for every instruction in the instruction set for the noted segments of the program 1833.

The MGPU method may alternatively be implemented in dedicated hardware such as one or more integrated circuits performing the MGPU functions or sub functions. Such dedicated hardware may include graphic processors, digital signal processors, or one or more microprocessors and associated memories.

Figure 4:
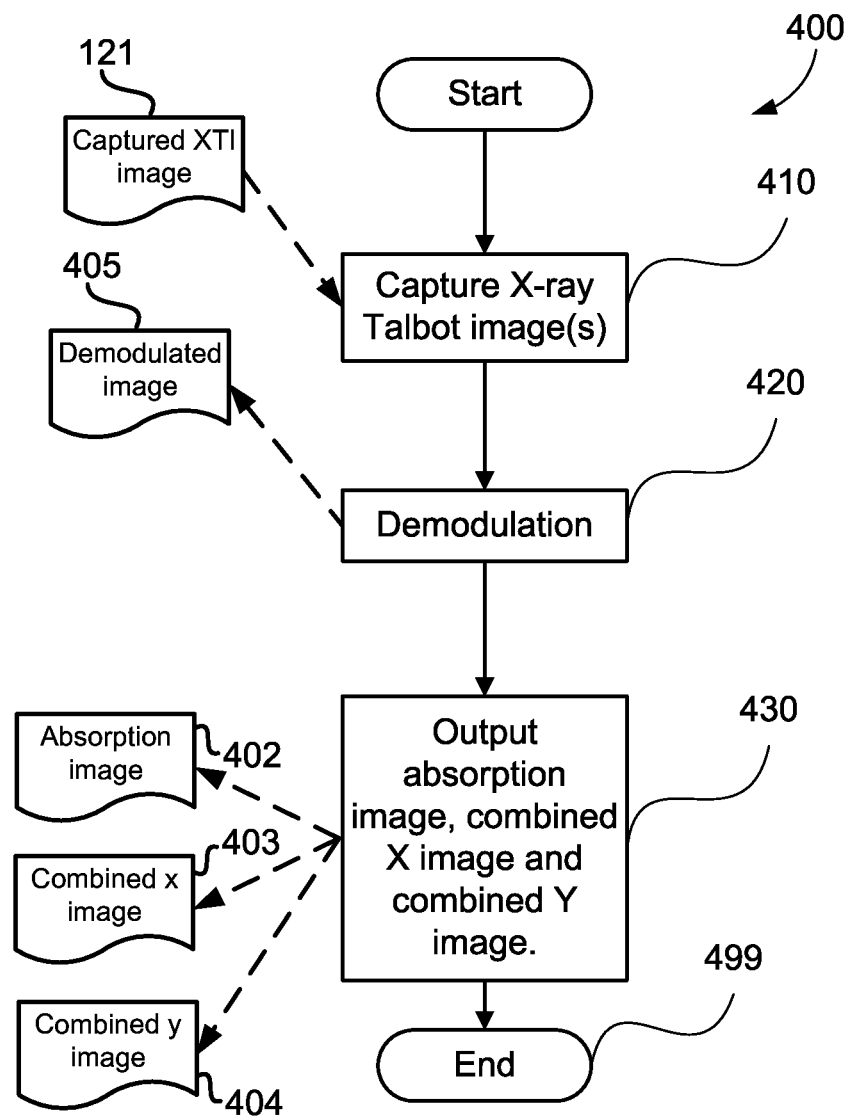
FIG. 4 is a flow chart of a demodulation process for X-ray Talbot interferogram images according to a MGPU arrangement.

FIG. 4 is a flow chart of a typical demodulation process for XTI images according to a MGPU arrangement 400. In FIG. 4, an XTI system such as 100 captures at least one XTI image 121 in a step 410. The captured XTI images 121 are then demodulated by the processor 1805 as directed by the MGPU software program 1833, using methods such as phase stepping or Fourier domain methods, in a following step 420, to produce the demodulated image 405 by removing the carrier signal due to the gratings. An output 430 of the demodulation step 420, which is the demodulated image 405, can be represented as three images (after combining the modulation and the phase images for each of the two directions, namely the horizontal direction x and vertical direction y), namely an absorption image a(r) (ie 402), a combined x image $c_x(r)$ (ie 403) and a combined y image $c_y(r)$ (ie 404). In particular, this MGPU arrangement focuses on reversing the phase wrapping effect in the XTI system, i.e., extracting the underlying phase information of the object from $c_x(r)$ and $c_y(r)$. The process 400 then terminates with an END step 499.

Figure 23:
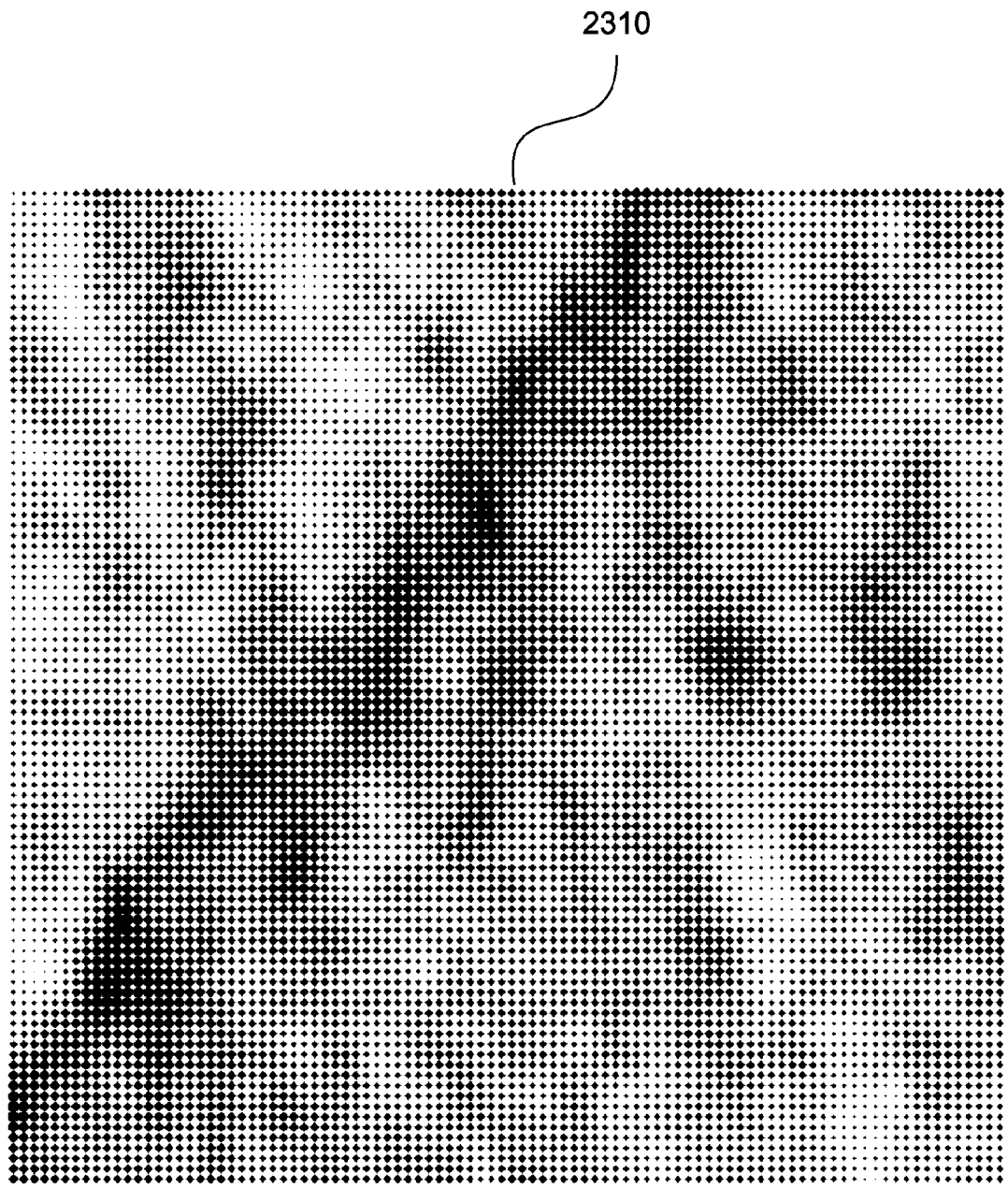
FIG. 23 shows an example of a 96×96 region of an XTI modulation image.
Figure 24:
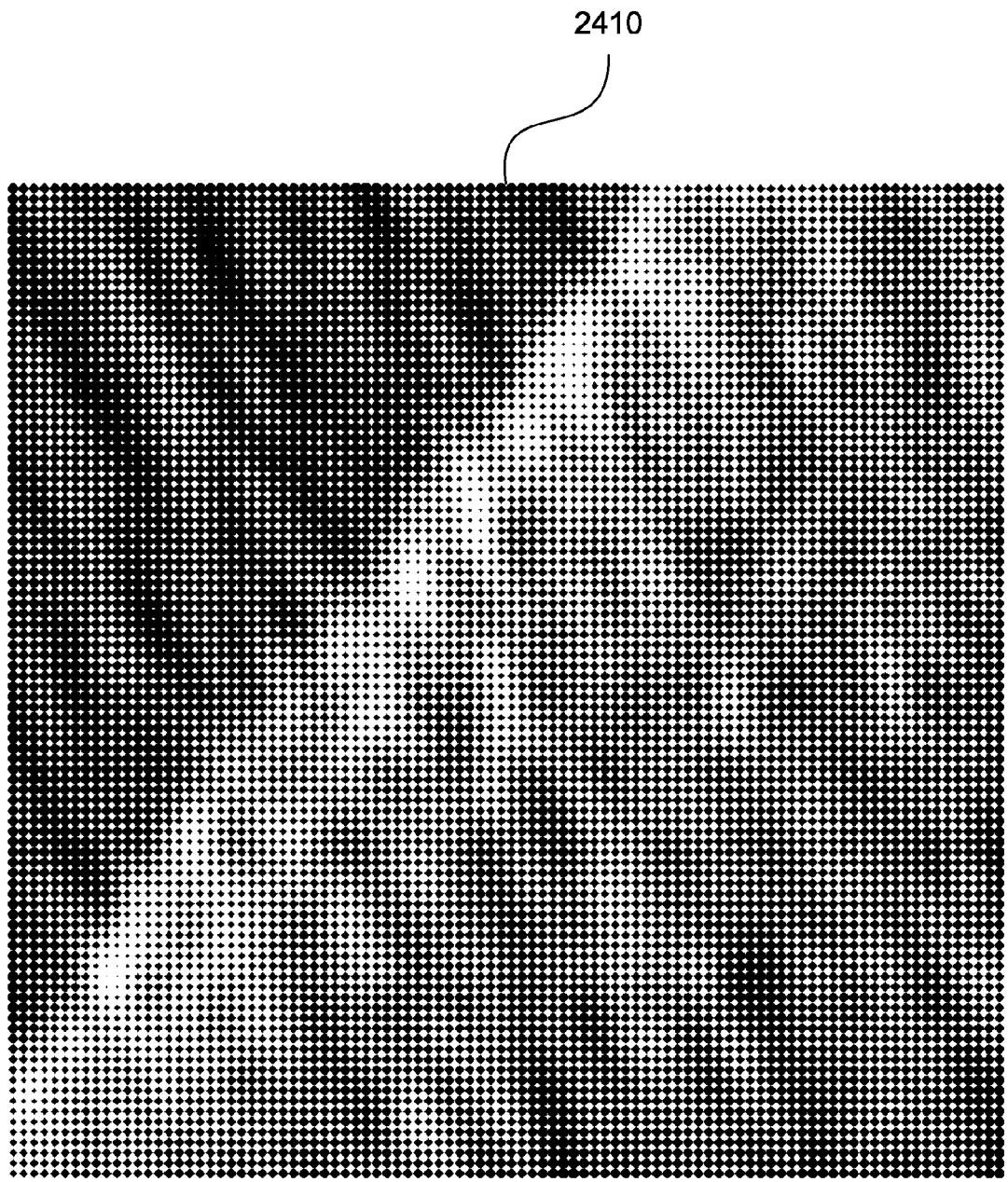
FIG. 24 shows an example of a 96×96 region of an XTI phase image

FIG. 23 shows an example 2310 of a modulation image of the moiré image (2310) $|c_x(r)|$, and FIG. 24 shows the corresponding phase image 2410 of the moiré image, arg $c_x(r)$.

Overview of the MGPU Arrangement

XTI arrangements such as the Talbot-Lau system shown in FIG. 1, produce high visibility moiré images even with a relatively large X-ray source. This is done by using the extra source grating G0 (ie 101), placed between the X-ray source 104 and the object 102 to generate an array of virtual sources. Each virtual source produces a clean moiré image with good visibility at a slightly shifted position on the sensor 140. The self-image 120 behind the phase grating 110 (ie G1) is in fact a sum of all these shifted clean moiré images (which are also referred to as "fringe images"). One side effect of the Talbot-Lau system is that the source grating 101 (ie G0) creates a convolution-like effect on the self-image 120. In particular, when a fringe image is shifted relative to and added to another fringe image with the same fringe period, their addition is constructive if they are in phase. If two fringe images are out of phase, for example, when they are shifted so that the peaks of the first image match the valleys of the second image, they cancel each other out.

When there is a discontinuity in the material in the object (ie. 102), such as the transition between bone and muscle or between glass and wood in the object 102 at a location r in one of the modulation images $m_x(r)$ or $m_y(r)$, the convolution-like effect described in the previous paragraph will add together two signals with similar amplitudes but, in the worst case, phases 180 degrees apart at the location of the sharp transition. That is, the modulation strength (amplitude) $m_x(r)$ or $m_y(r)$ at the location r will quickly drop and come back up if there is a sharp phase edge at the location r. As a corollary, when there is a sudden dip or local minimum in the $m_x(r)$ or $m_y(r)$ image, there likely is a phase edge at the location of the local minimum.

This can be seen in the example modulation image 2310, in which a line of minimum modulation can be seen extending from a south-west position in the image towards the north. This line of minimum modulation is associated with a change in the phase image 2410, with an increase in phase moving across the modulation minimum in a south-easterly direction.

Using the modulation minimum, one can distinguish between a real phase edge and a phase discontinuity generated by phase wrapping. In this specification, a 'phase discontinuity' can be caused by either a real phase edge or a phase wrapping effect. The MGPU arrangements aim to use amplitude modulation information from the demodulated XTI image 405 to help identify the location of real phase edges, estimate the height of the phase edges and avoid error propagation in phase unwrapping.

MGPU Arrangement No. 1

Figure 5:
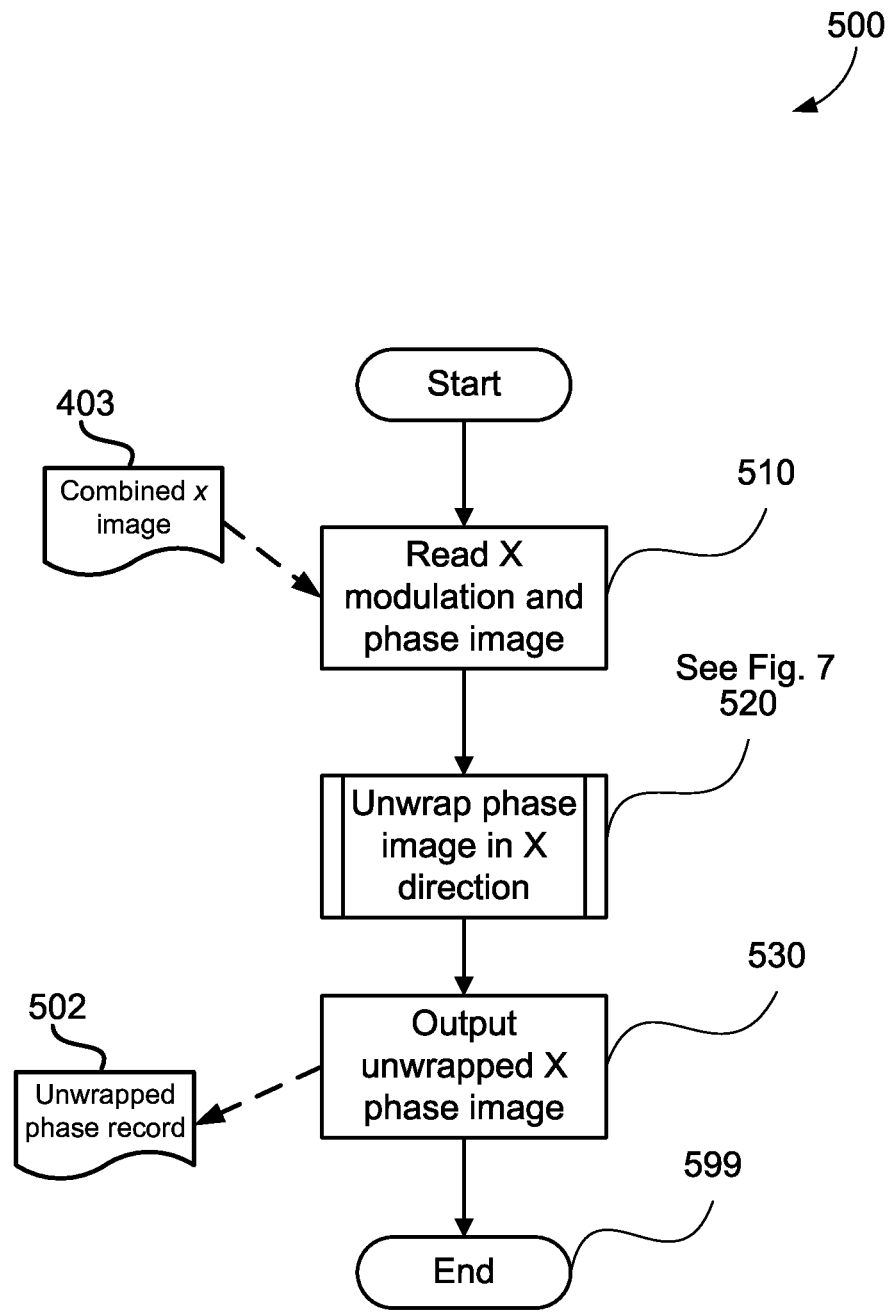
FIG. 5 is a flow chart of a method of phase unwrapping in x direction using modulation information in the X-ray Talbot interferometry according to one MGPU arrangement.
Figure 6:
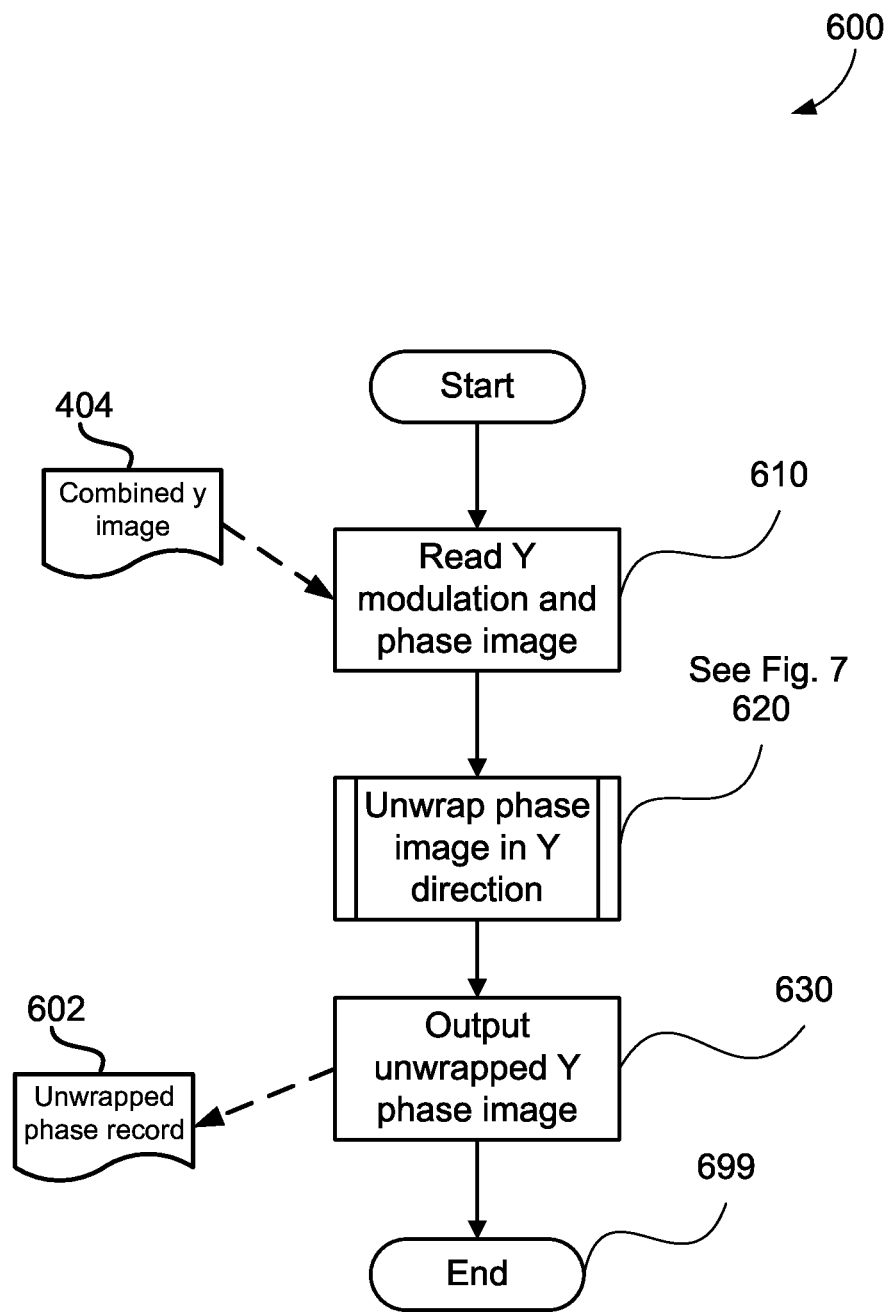
FIG. 6 is a flow chart of a method of phase unwrapping in y direction using modulation information in the X-ray Talbot interferometry according to one MGPU arrangement.

FIG. 5 and FIG. 6 depict the phase unwrapping process according to the MGPU arrangement, applied independently to the combined x image $c_x(r)$ and the combined y image $c_y(r)$.

FIG. 5 is a flow chart of a method 500 for phase unwrapping in the x direction using amplitude modulation information in the X-ray Talbot interferometry according to one MGPU arrangement. A step 510 reads the combined x image $c_x(r)$ (ie 403). A following step 520, described hereinafter in more detail with reference to FIG. 7, applies the phase unwrapping method according to the MGPU arrangement that makes use of the amplitude modulation information. A following step 530 outputs unwrapped results 502 comprising an unwrapped phase record, described hereinafter in more detail with reference to 1323 in FIG. 13 for example.

FIG. 6 is a flow chart of a method 600 for phase unwrapping in the y direction using amplitude modulation information in the X-ray Talbot interferometry according to one MGPU arrangement. A step 610 reads the combined y image $c_y(r)$ (ie 404). A following step 620, described hereinafter in more detail with reference to FIG. 7, applies the phase unwrapping process according to the MGPU arrangement. A following step 630 outputs unwrapped results 602. The unwrapped results in the x direction (ie, 502) and the y direction (ie, 602) are both phase images that are estimation of the underlying object phase $\xi_x(r)$ and $\xi_y(r)$.

The step 520 in FIG. 5 and the step 620 in FIG. 6 are essentially the same process, applied in different directions. Note that in this MGPU arrangement, the phase unwrapping process to recover the x phase uses the combined x image $c_x(r)$ only and the phase unwrapping process to recover the y phase uses the combined y image $c_y(r)$ only. That is, only the x modulation $m_x(r)$ and the wrapped x phase $\xi_x(r)$ are used to recover the unwrapped x phase. Similarly, only the y modulation $m_y(r)$ and the wrapped y phase $\xi_y(r)$ are used to recover the unwrapped y phase. For example, if there is a modulation minimum at a location r in the y modulation image $m_y(r)$ but not in the x modulation image $m_x(r)$, the y phase unwrapping step 620 will use this modulation minimum at the location r to help unwrapping the y phase. The combined x image $c_x(r)$, in other words the x modulation $m_x(r)$ and the wrapped x phase image $\xi_x(r)$, are not involved in this case.

Figure 7:
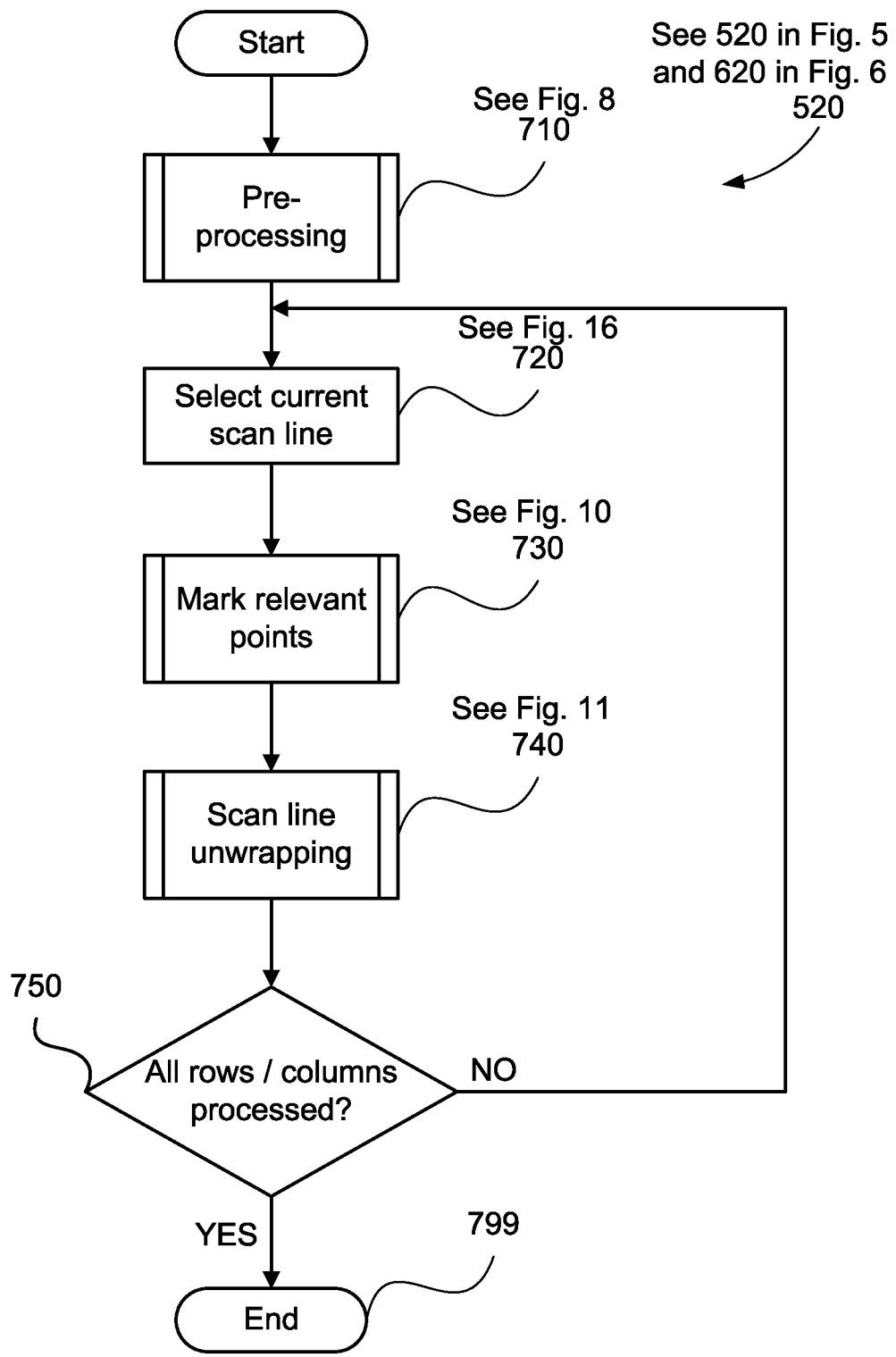
FIG. 7 is a flow chart of a phase unwrapping method as used in the processes of FIG. 5 and FIG. 6.

FIG. 7 is a flow chart of a phase unwrapping method 520 as used in the respective steps 520 and 620 in the respective processes 500 and 600 of FIG. 5 and FIG. 6. A step 710, described hereinafter in more detail with reference to FIG. 8, pre-processes the combined x image $c_x(r)$ or the combined y image $c_y(r)$ to reduce noise. A following step 720, described hereinafter in more detail with reference to FIG. 16, selects one row (or column, depending on whether it is processing the combined x image $c_x(r)$ or the combined y image $c_y(r)$) of the XTI image as the current scan line. A following step 730, described hereinafter in more detail with reference to FIG. 10, marks pixel locations on the current scan line as relevant points for phase unwrapping. A following step 740, described hereinafter in more detail with reference to FIG. 11, applies a scan line phase unwrapping method according to the MGPU arrangement to the current scan line. A following step 750 checks to determine if all rows (or columns) in the phase image have been processed. If this is not the case, the process 520 follows a NO arrow to the step 720. If the step 750 returns a logical TRUE value, the process 520 follows a YES arrow to an END step 799.

In this MGPU arrangement, each pixel location in the captured images 121 is processed independently without consideration of its neighbouring pixels. Therefore the location parameter r is omitted in the remainder of this description for the sake of simplicity. For example, the x modulation image $m_x(r)$ is henceforth referred to as $m_x$ and the y modulation image $m_y(r)$ is henceforth referred to as $m_y$. Similarly, the x phase image $\xi_x(r)$ is henceforth referred to as $\xi_x$ and the y phase image $\xi_y(r)$ is henceforth referred to as $\xi_y$.

The step 720 selects the current scan line for processing. The steps 730 and 740 find points of interest (relevant points) on the current scan line and apply a scan line (one dimensional) phase unwrapping method to the current scan line using the phase image $\xi_x$ or the phase image $\xi_y$ depending upon the direction in which the phase unwrapping is carried out. If x phase unwrapping is carried out, the process 500 in FIG. 5 is used and the current scan line is a horizontal line in $\xi_x$. If y phase unwrapping is carried out, the process 600 in FIG. 6 is used and the current scane line is a vertical line in $\xi_y$. This is described hereinafter in more detail with reference to FIG. 16.

Because the step 730 and the step 740 are directed to one scan line only, and because the scan line phase unwrapping process is the same for horizontal and vertical scan lines, ie the scan line is a vertical line when processing the combined y image $c_y(r)$ and it is a horizontal line when processing the combined x image $c_x(r)$, the remainder of the description of the MGPU arrangement focuses on the x direction only. Any processing directed to the y direction is performed in exactly the same fashion as in the x direction, except that the results are unwrapped y phase and not unwrapped x phase.

After selecting the current scan line in the step 720, the step 730 marks relevant points on the current scan line for further processing. Using the combined x image $c_x(r)$ as an example, a point p is considered to be a relevant point if there is either (i) a local modulation minimum (ie a dip in the modulation strength) in the modulation image $m_x$, and/or (ii) a positive discontinuity in the phase image $\xi_x$ and/or (iii) a negative discontinuity in the phase image $\xi_x$ at the location p. The points (i), (ii), and (iii) are respectively labelled 'mod', 'pos', and 'neg'. Using the combined x image $c_x(r)$ as an example, a positive discontinuity is defined as a sudden change in the x phase at a point on the scan line, where the phase value on the right of the point is greater than the value on the left. A negative discontinuity is defined as a sudden change in the x phase at a point on the scan line where the phase value on the right of the point is smaller than the value on the left. This is described hereinafter in more detail with reference to FIG. 10.

Once the relevant points are labelled as 'mod', 'neg' or 'pos' in the step 730, the scan line phase unwrapping algorithm is applied to the current scan line by the step 740, described hereinafter in more detail with reference to FIG. 11. The general idea of the scan line phase unwrapping algorithm is that for each scan line in the appropriate modulation image $m_x$, $m_y$ and the phase image $\xi_x$, $\xi_y$, a corresponding one-dimensional unwrapped phase signal is generated in the respective x or y direction, using information from the current scan line of the modulation image ($m_x$ or $m_y$) and the phase image ($\xi_x$ or $\xi_y$).

Figure 8:
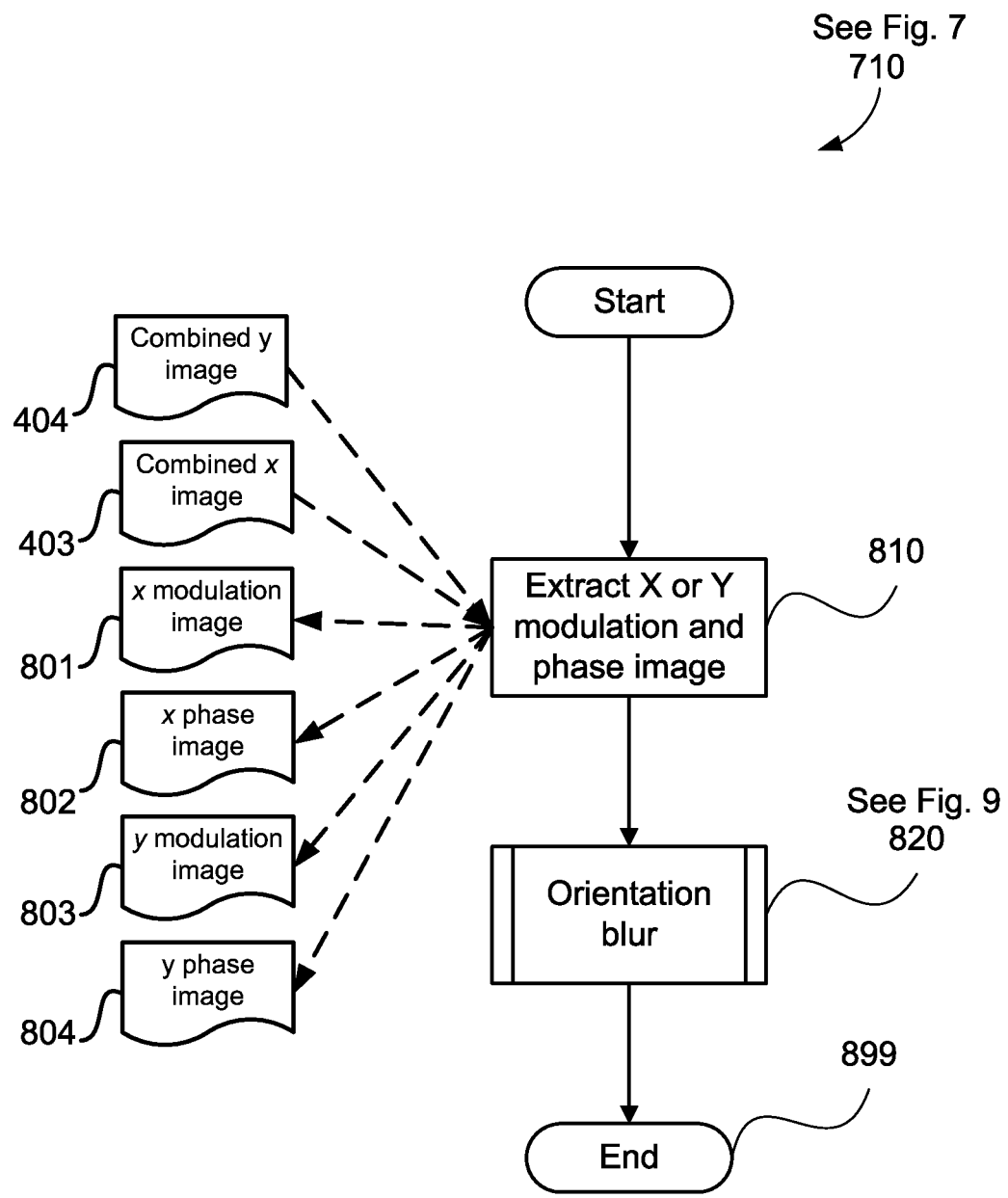
FIG. 8 is a flow chart of a pre-processing step as used in FIG. 7.

FIG. 8 is a flow chart of a pre-processing step 710 as used in FIG. 7. A step 810 separates (ie decomposes) the combined x image $c_x(r)$ (ie 403) or the combined y image $c_y(r)$ (ie 404) into respective modulation images $m_x$, $m_y$ (ie 801, 803) and phase images $\xi_x$, $\xi_y$ (ie 802, 804). As previously described, the 'modulation image' is referred to as $m_x$ or $m_y$ in Equation (1) and the 'phase image' is referred to as $\xi_x$ or $\xi_y$, which can be derived from the phase functions $\phi_x$ or $\phi_y$ in Equation (1). The values of the 'modulation image' are normalised in this MGPU arrangement. Accordingly, a nominal value of 1.0 represents no attenuation of modulation, as will occur in regions of the image containing no object. A nominal value of 0.0 represents a complete extinguishment of the modulation strength as will occur when the object absorbs most of the X-ray energy and no signal is captured at a particular pixel position. A following step 820, described hereinafter in more detail in regard to FIG. 9, applies a procedure referred to as 'orientation blur' to the modulation image $m_x$ or $m_y$ to reduce noise in the modulation image $m_x$ or $m_y$.

Figure 9:
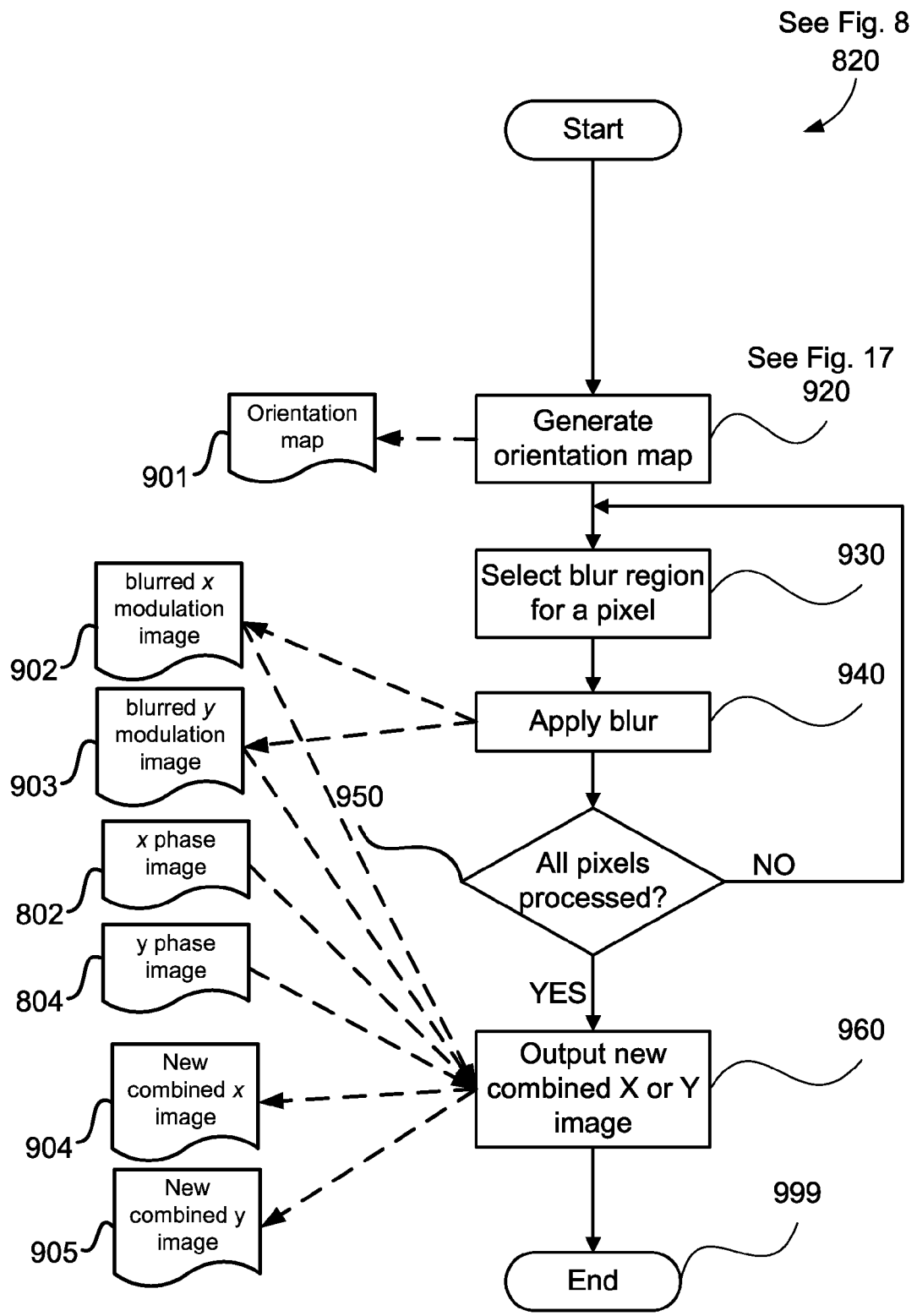
FIG. 9 is a flow chart illustrating a orientation blur method as used in FIG. 8.

FIG. 9 is a flow chart illustrating an orientation blur method 820 as used in FIG. 8. A step 920 generates an orientation map 901 by determining the orientation and energy of each pixel location in the x modulation image $m_x$ or the y modulation image $m_y$. One typical method for calculating orientation is to calculate the direction of the gradient in the x modulation image $m_x$ or the y modulation image $m_y$ at the pixel location using finite difference and define the direction perpendicular to the gradient direction as the 'orientation'. The orientation of a pixel location is described hereinafter in more detail with reference to FIG. 17. The energy of a pixel location is defined in the MGPU arrangements as the square of the gradient strength at the pixel location, which is an estimate of noise level.

Figure 17:
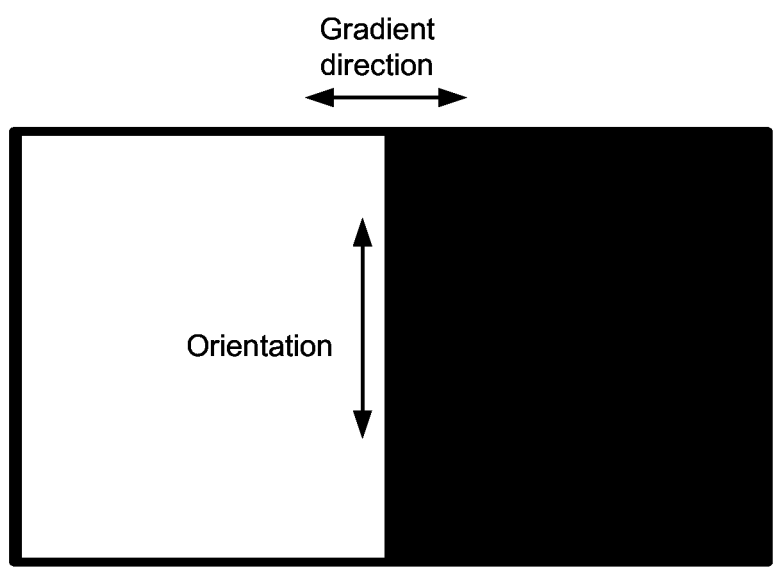
FIG. 17 illustrates an example of orientation of a pixel and a gradient direction.

FIG. 17 illustrates an example of orientation of a pixel and a gradient direction. The sudden change in intensity in FIG. 17 from bright (left part of the rectangle) to dark (right part of the rectangle) gives a large 'energy' along the marked orientation although the gradient direction is in fact perpendicular to the orientation. With the orientation map 901, an edge preserving blur can be applied to the x or y modulation image so that the blur happens along the orientation to avoid smoothing important edges.

Returning to FIG. 9, a following step 930 selects a blur region for each pixel in the x modulation image $m_x$ (ie 801) or the y modulation image $m_y$ (ie 803) according to the orientation map 901. In this MGPU arrangement, the blur region selected by the step 930 includes pixel locations on a straight line in the direction of the orientation of the pixel in question in the orientation map 901, centred at the current pixel location.

Figure 21:
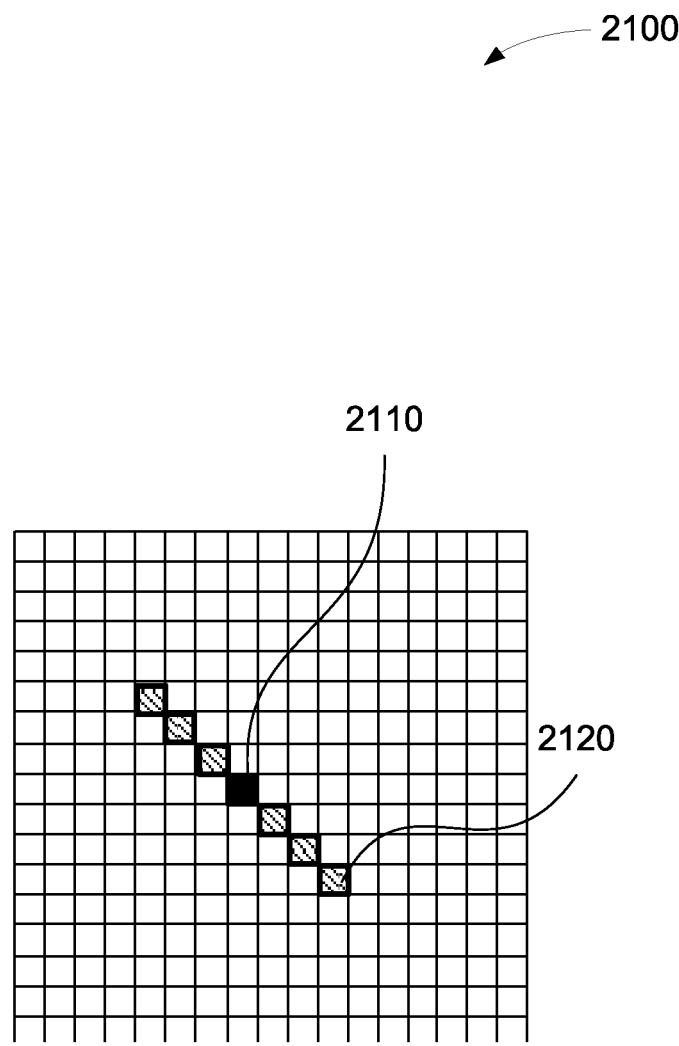
FIG. 21 shows an example of a blur region.

FIG. 21 shows an example of such a blur region, where 2110 indicates the current pixel location and the shadowed pixels on a straight line at 135 degrees as depicted by 2120 represent the blur region. The size of the blur region in FIG. 21 is the length of the line and it is proportional to the energy value associated with the pixel in question in the orientation map 901. In other words, the larger the energy value for a pixel, the longer the line is, therefore the more blur is applied for this pixel.

A following step 940 uses a box blur process (or other averaging process) in the blur region to blur the current pixel, thus constructing, on a pixel-by-pixel basis, a blurred x modulation image 902 and a blurred y modulation image 903. A box blur process is implemented by an image filter in which each pixel in the resulting image has a value equal to the average value of its neighboring pixels in the input image. It is a form of low-pass ("blurring") filter and is a convolution. The aforementioned choice of blur orientation and blur region size ensures that the blur is applied along edges of objects in the modulation image, and not across edges. The local minima in the modulation image should be blurred more than other pixel locations due to the high energy (gradient) values associated with the local minima. This makes it possible to reduce noise without compromising the contrast that is present in the x modulation image $m_x$ or the y modulation image $m_y$. A following step 950 determines if all pixels in the modulation image have been processed. If this is the case, the process 820 follows a YES arrow to a step 960 which recombines the blurred version 902, 903 of the respective x modulation image $m_x$ (801) or x modulation image $m_y$ and the corresponding phase image $\xi_x$ or $\xi_y$ to form a new combined x image 904 or a new combined y image 905. The phase images $\xi_x$ or $\xi_y$ (ie 802, 804) and the blurred versions 902, 903 of the respective modulation images $m_x$ or $m_y$ formed at the step 960 are used in the step 730 in FIG. 7 to determine relevant points for phase unwrapping, as described hereinafter in more detail with reference to FIG. 10.

Figure 16:
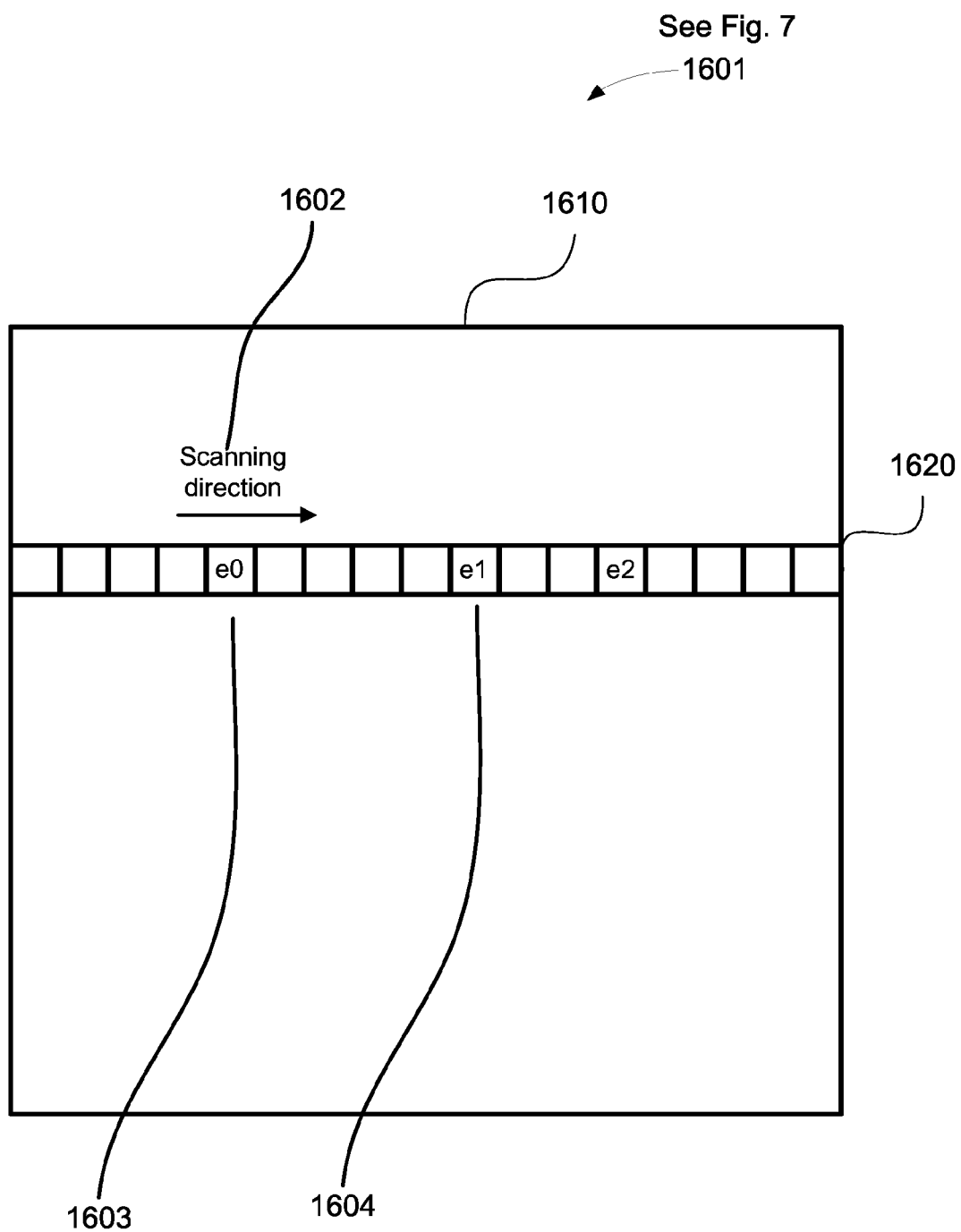
FIG. 16 shows an example of a scan line in one of the two processing directions according to one MGPU arrangement.

FIG. 16 illustrates an example 1601 of a scan line in one of the two processing directions according to one MGPU arrangement. FIG. 16 depicts an example of selecting, by the step 720 in FIG. 7, a scan line in the x direction. A reference numeral 1610 can depict the x modulation image $m_x$ or the x phase image $\xi_x$ since they have the same dimension. A reference numeral 1620 depicts the current scan line selected for processing by the step 720. In the example in FIG. 16, the current scan line 1620 includes all pixel locations such as e0 (ie 1603), e1 (ie 1604) in the row (ie in the x direction). The scanning direction 1602 is from left to right. In FIG. 16, the pixel e0 (ie 1603) is 'before' the pixel e1 (ie 1604) in scan order and e1 is 'before' a pixel e2 in scan order. The pixel e0 is 'on the left' of e1 and the pixel e1 is 'on the right' of e0.

Figure 10:
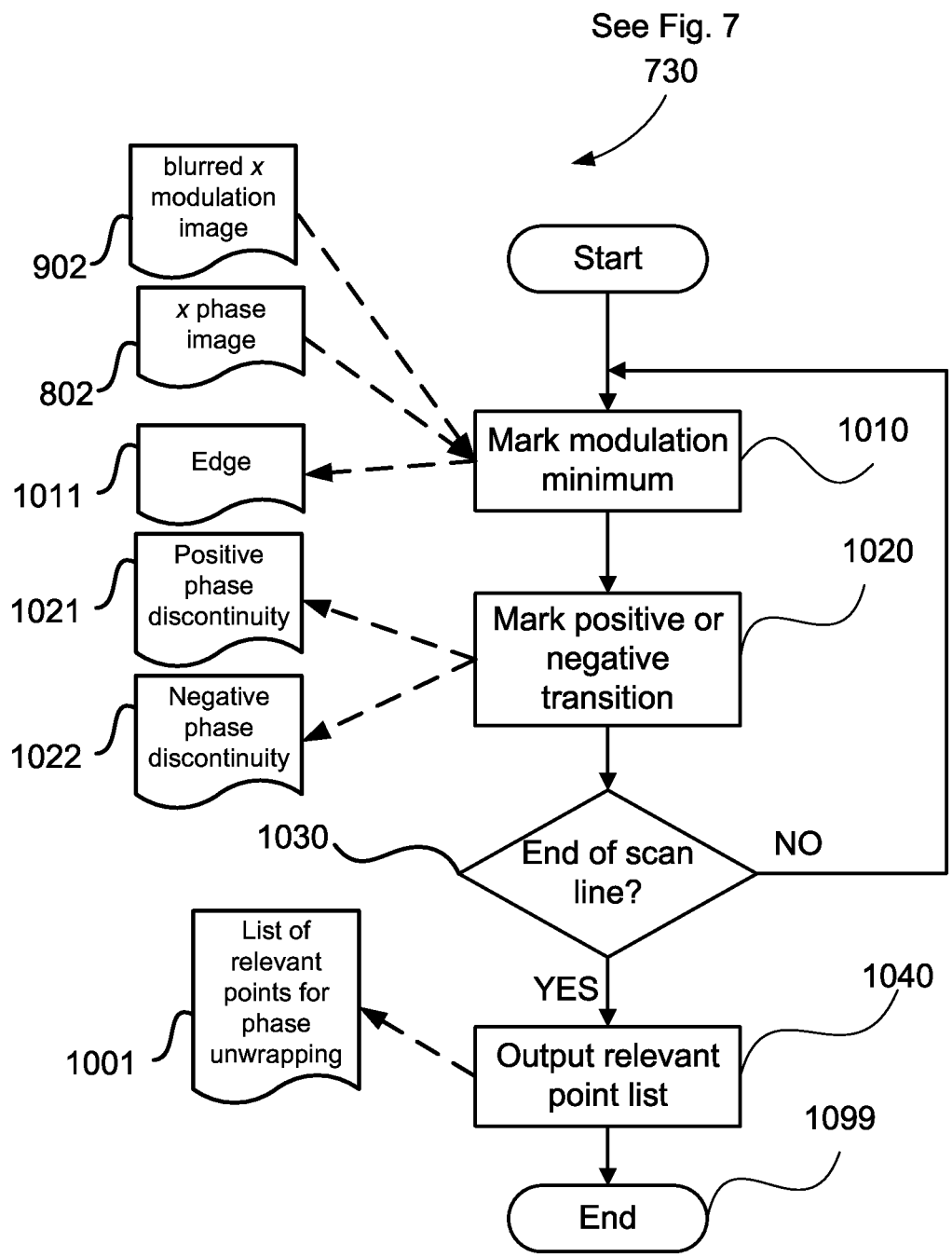
FIG. 10 is a flow chart illustrating a process of marking relevant points as used in FIG. 7.

FIG. 10 is a flow chart illustrating a process 730 of marking relevant points as used in FIG. 7. For simplicity the process 730 is described with references to the x modulation image $m_x$ and the x phase image $\xi_x$ only, however, the same process can be applied to y images to determine relevant points in y direction. The relevant points are selected from the x phase image $\xi_x$ (ie 802), and the blurred x modulation image $m_x$ (ie 902) that is formed by using the "orientation blur" step 940 described with reference to FIG. 9. Using the combined x image $c_x(r)$ (ie 403) as an example input, in the step 1010, the current scan line from the blurred x modulation image 902 is processed to find local minima in modulation strength which might indicate the presence of an edge 1011 in the object 102. A local minimum on the current scan line is identified if the modulation value of the pixel in question, when compared with its immediate neighbours on the left and on the right, is significantly lower than that of its immediate neighbours on the left and on the right. To only target local minima which are likely to indicate an edge, a modulation value should be below a threshold to be regarded as a local minimum. With the normalization as described above, it has been found that a threshold value of 0.3 gives good results. These local minima are then marked as relevant points and labelled as 'mod'.

A following step 1020 detects positive discontinuities 1021 and negative discontinuities 1022 using phase differences along the current scan line from the x phase image $\xi_x$ (ie 802) and marks the detected discontinuities, being positions of substantial change in the phase image, in the x phase image as either negative transitions (labelled 'neg') if it is a negative discontinuity or positive transitions ('pos') if it is a positive discontinuity. As previously noted, a positive discontinuity is defined as a sudden change in the x phase at a point on the scan line, where the phase value on the right of the point is greater than the value on the left, and a negative discontinuity is defined as a sudden change in the x phase at a point on the scan line where the phase value on the right of the point is smaller than the value on the left. A following step 1030 then determines if the processing has reached the end of the scan line. If this is the case, the process 730 follows a YES arrow to a step 1040 that outputs a relevant list 1001 of points for phase unwrapping for the current scan line. This relevant point list is an ordered list of pixel locations and corresponding labels such as 'mod', 'neg' or 'pos'. The process 730 is then directed to an END step 1099 and terminates. Returning to the step 1030, if the step returns a FALSE value, then the process 730 follows a NO arrow back to the step 1010.

Figure 11:
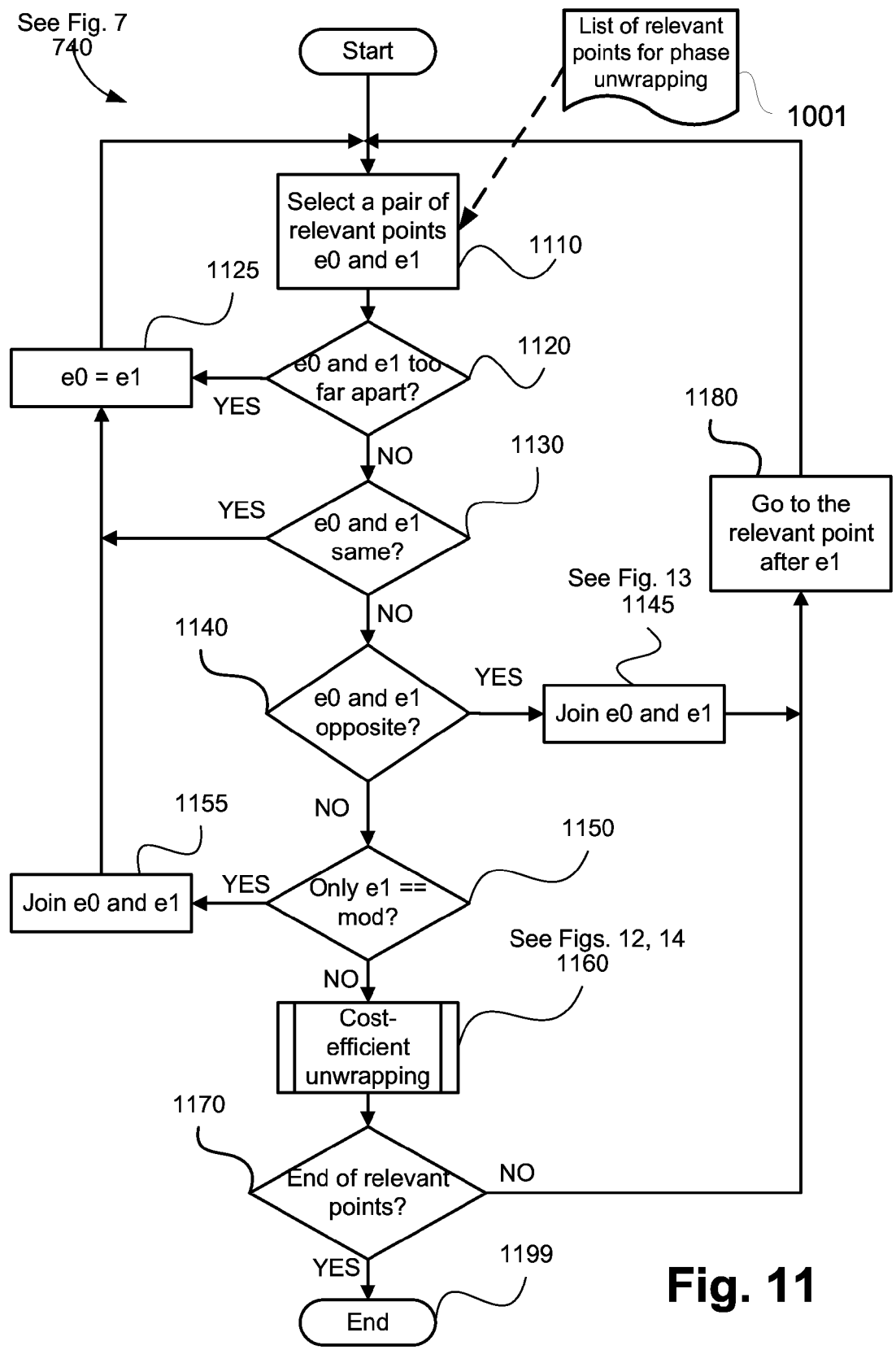
FIG. 11 is a flow chart illustrating a scan line phase unwrapping process as used in FIG. 7 according to one MGPU arrangement.

FIG. 11 is a flow chart illustrating a scan line phase unwrapping process 740 as used in FIG. 7 according to one MGPU arrangement. A step 1110 selects a pair of neighbouring relevant points (ie pixels in one MGPU arrangement) e0 and e1 from the relevant point list 1001 of the current scan line, where e0 is before e1 in the scan order. It should be noted that e0 is not necessarily the first relevant point on the current scan line, although it is the first relevant point for the current run of the current scan line. A run includes a group of relevant points on the current scan line that are considered for joining. In other words, relevant points in the same run are connected to each other by the same phase discontinuity or the same phase wrapping effect. Each scan line can have several runs. A run ends when a decision has been made to join two or more relevant points in some manner. For example, step 1155 and 1180 end a run by joining the current e0 and e1. Similarly, a run ends after step 1280, 'join segments with low cost', in FIG. 12. A new run starts with the next relevant point in the scan order.

A following step 1120 determines if these two relevant points are too far apart on the scan line. This is determined on the basis of a threshold that is determined based on modelling the particular XTI system 100 in question. The value of the threshold depends mainly on the fringe period of the captured XTI image. For example, with a fringe period of 32 pixels per fringe, if the two relevant points are more than 10 pixels apart, they are considered too far apart. If the distance between e0 and e1 is greater than the threshold, ie if the step 1120 returns a logical TRUE value, then the process 740 follows a YES arrow to a step 1125. This step sets a new e0 to the current e1, and marks the next relevant point on the current scan line as the new e1. The process 740 is then directed back to the step 1110. This check 1120 helps avoid joining two relevant points that are physically far apart, since the phase wrapping effect is assumed to create relatively short segments of the underlying phase signal compared to the segments created by real phase edges.

Returning to the step 1120, if e0 and e1 are close enough to be considered for joining, the process 740 follows a NO arrow to a step 1130 that determines if e0 and e1 are both 'mod', or both 'neg' or both 'pos'. If they are, then control is directed to the step 1125 which starts a new pair of relevant points at the current e1. This is because a sequence of homogeneous labels indicates a high probability of noise. This MGPU arrangement eliminates such noise by picking only the last relevant point in such a sequence. The aim of this MGPU arrangement is to join 'mod' point with 'pos' or 'neg' points because such an arrangement of relevant points would indicate phase discontinuity caused by edges of the object.

Returning to the step 1130 if e0 and e1 have different labels, then control follows a NO arrow to a step 1140 that determines if e0 and e1 are opposite, i.e., if one of them is 'pos' and the other 'neg'. If this is the case, control follows a YES arrow to a step 1145 that joins e0 and e1, as described hereinafter in more detail with reference to FIG. 13, and the process 740 is directed to a step 1180, where the relevant point after the current e1 on the current scan line is selected as the new e0 and a new pair is started. The process 740 is then directed back to the step 1110.

For purpose of this description, the term 'join' is used as a synonym for phase unwrapping. Phase wrapping produces discontinuities and 'join' refers to the process of eliminating these discontinuities by connecting (joining) two segments of phase signals. If the step 1140 determines that e0 and e1 do not have opposite labels, since they are already known to be different at this stage (ie the step 1130 checks if they are the same), this means that one and only one of the two relevant points is labelled 'mod'. The process 730 thus follows a NO arrow from the step 1140 to a step 1150 that determines which one of e0 and e1 is 'mod'. If e1 is 'mod', control follows a YES arrow to a step 1155 that joins e0 and e1 and the process 730 is directed to the step 1125 again and starts a new pair of relevant points at the current e1. Returning to the step 1150, if e0 is the one that's labelled 'mod', control follows a NO arrow to a step 1160 that applies a cost-efficient unwrapping method, as described hereinafter in more detail with reference to FIG. 12. The meaning of 'cost-efficient' will be demonstrated through a hypothetical example in FIG. 14.

The process 740 is then directed to a step 1170 that determines if the process 730 has reached the end of the relevant point list for the current scan line. If this is the case, the process 730 follows a YES arrow to an END step and terminates. If the step 1170 returns a FALSE value, then the process 740 follows a NO arrow to the step 1180 to start a new pair.

Figure 13:
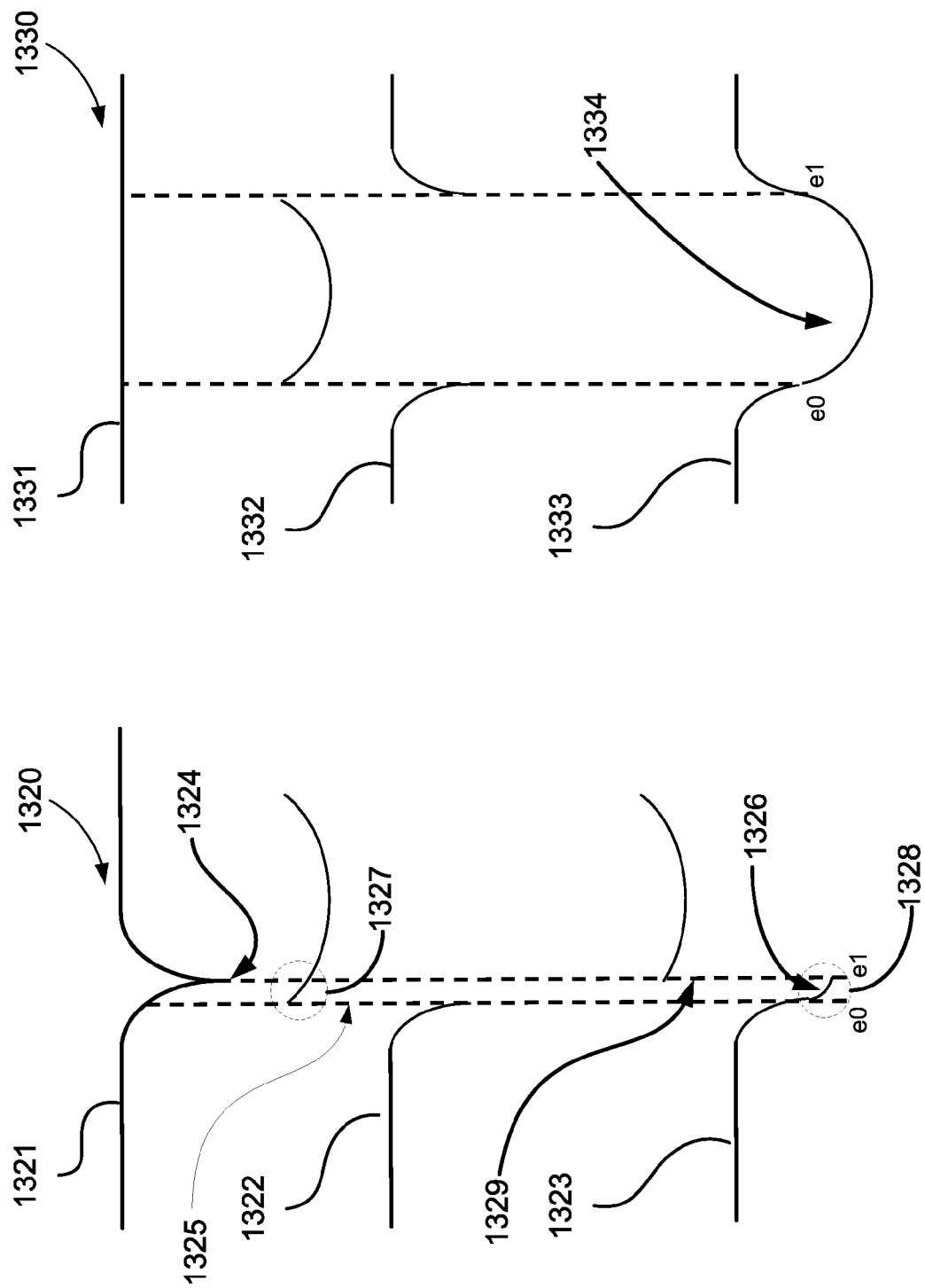
FIG. 13 illustrates the joining of phase signals as used in FIG. 11.

FIG. 13 illustrates the joining of phase signals as used in FIG. 11. In particular, the 'join e0 and e1' steps 1145 and 1155 are described with the aid of two hypothetical examples.

An example 1320 illustrates the joining process in the step 1155, where the case e1 is 'mod' and e0 is 'pos' is handled. A top signal 1321 depicts a current scan line in the x modulation image $m_x$. A reference numeral 1322 depicts the current scan line in the (wrapped) x phase image $\xi_x$, and a reference numeral 1323 depicts the unwrapped phase record for the current scan line 1321. A modulation minimum can be seen at the pixel e1, as shown at 1324 in the signal 1321. In 1322, there is a positive transition 1325 at the location of the pixel e0. Since the location of the modulation minimum 1324 is considered the true location of the phase edge, a segment 1327 between e0 and e1 in 1322 which is in the vicinity of the modulation minimum 1324 is shifted down, as depicted at 1326, thus refining the position of the discontinuity so that the discontinuity after phase unwrapping 1329 falls on e1, to correspond with the modulation minimum 1324, as depicted in 1323. The segment 1327 is thus adjusted by being shifted downwards. In this example, by $2\pi$ (ie one cycle). In other examples, described hereinafter in more detail for example in regard to FIG. 15, such a segment may be shifted by multiple cycles (ie multiple values of $2\pi$).

An example 1330 illustrates the joining process in the step 1145. A top signal 1330 depicts a current scan line in the x modulation image $m_x$. A reference numeral 1332 depicts the current scan line in the x phase image $\xi_x$, and a reference numeral 1333 depicts the wrapped phase for the current scan line. In 1330, there is no local minimum in the modulation image 1331. The pixels e0 and e1 have opposite labels as determined by the step 1140. Therefore, it is assumed that there is no real phase edge, and that any discontinuity is thus due only to the phase wrapping effect. Accordingly, the phase wrapping effect can be removed by shifting the segment between e0 and e1 down by $2\pi$ as depicted by 1334 to produce a smooth signal, as shown in 1333.

Figure 12:
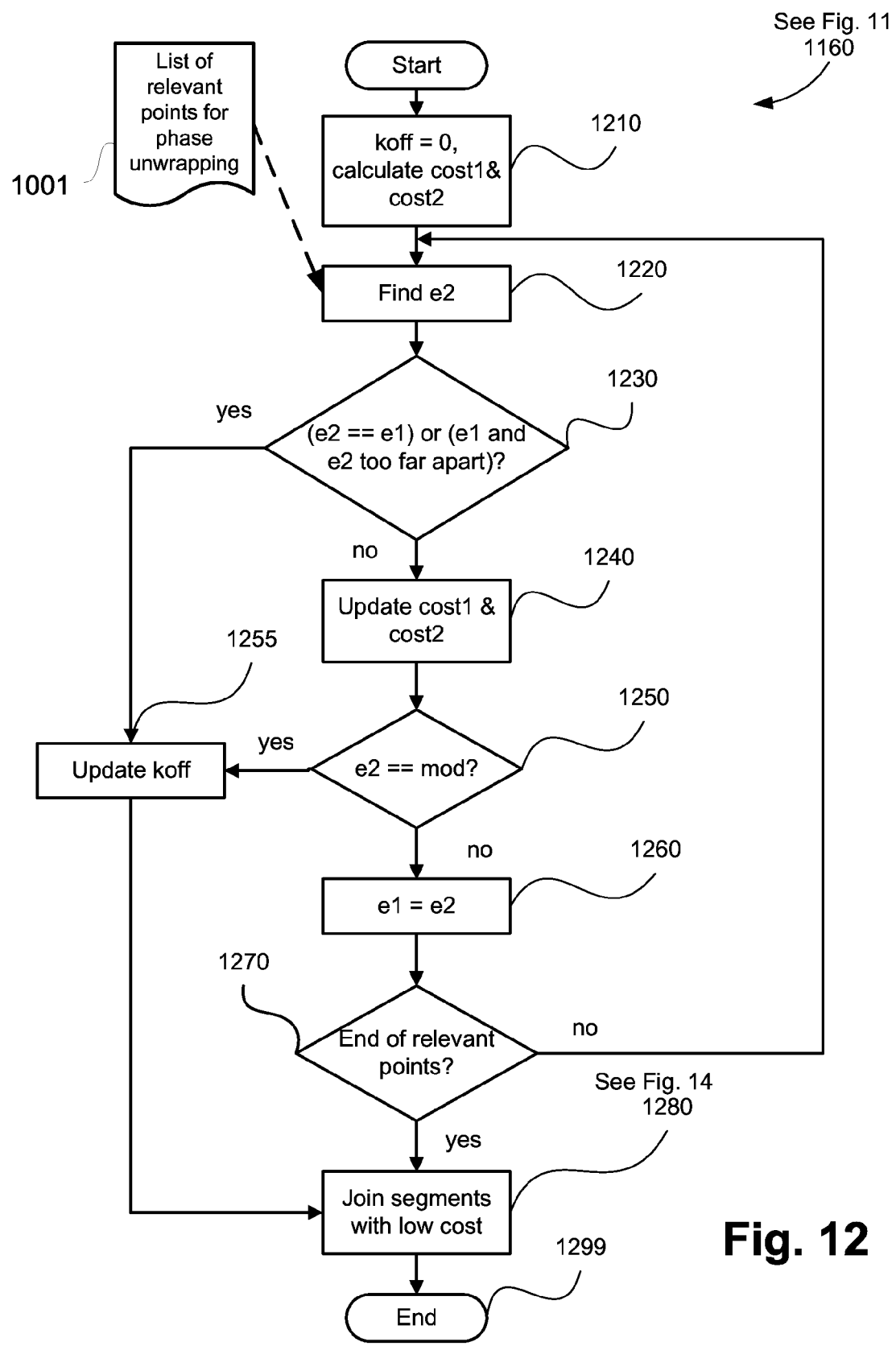
FIG. 12 is a flow chart of a cost efficient phase unwrapping process as used in FIG. 11 according to one MGPU arrangement.

FIG. 12 is a flow chart of a cost efficient phase unwrapping process 1160 as used in FIG. 11 according to one MGPU arrangement. A step 1210 initializes variables koff, cost1 and cost2 where koff is either 0 or 1 and cost1 and cost2 are defined using number of pixels. The variable koff is set to zero initially, the variable cost1 is initialized to the distance on the scan line between e0 and e1, and the variable cost2 is set to zero. e0 is the starting point of the current run. There can be more than one run in the current scan line. Each run deals with one phase edge or phase unwrapping problem. There can be multiple edges or phase wrapping point in a scan line. A following step 1220 then finds the next point in scan order e2 from the relevant point list 1001 of the current scan line. It is noted that by the time the process 730 in FIG. 11 performs the step 1160, the step 1150 has been performed, ensuring that the value of e0 is 'mod' and the value of e1 is either 'neg' or 'pos'.

A following step 1230 checks if e2 has the same label as e1, which means that the sequence (e0, e1, e2) is a sequence having respective labels ('mod', 'neg', 'neg') or ('mod', 'pos', 'pos') or if e1 and e2 are too far apart. Based upon the proposition that two consecutive 'pos' or 'neg' values indicates noise, if the step 1230 returns a logical TRUE value, then the process 1160 follows a YES arrow, thus ignoring the second 'pos' or 'neg' and terminates this run of cost-efficient unwrapping, and is directed to a following step 1255, where koff is set to either 0 or 1 depending on the number of relevant points between e0 and e2. Initially, ie at the commencement of the process 1160, the number of relevant points between e0 and e2 is 1 because e2 is initially the relevant point immediately after e1 in scan order and e1 is the relevant point immediately after e0 in scan order. However, as the process 1160 progresses, e1 and e2 are updated (by a step 1260) by setting the current e2 to be e1 and the relevant point after the current e2 as the new e2. This means that at a certain stage in the process 1160, at the step 1160 the number of relevant points between e0 and e2 can be greater than 1. In the step 1255, if the number of relevant points between e0 and e2 is odd, koff is set to 0, otherwise koff f is set to 1.

After updating koff in the step 1255, the process 1160 is directed to a step 1280 to unwrap the phase by joining low cost segments, as described hereinafter in more detail with reference to FIG. 14. Returning to the step 1230, if e1 and e2 are far apart, the process 1160 again follows the YES arrow and the run ends, with koff being updated in the step 1255 and thereafter the process 1160 is directed to the step 1280. Returning to the step 1230, if neither of the two conditions are satisfied, the process 1160 follows a NO arrow to a step 1240 which updates cost1 and cost2 by adding the distance between e1 and e2 to either cost1 or cost2 depending on the number of relevant points between e0 and e2. Because e1 and e2 are constantly updated by moving them to the next relevant point on the scan line, if the number of relevant points between the current e2 and e0 is an odd number, the distance between e1 and e2 is added to cost2, otherwise the distance is added to cost1. A following step 1250 then checks to determine if e2 is 'mod'. If this is the case, the process 1160 follows a YES arrow to the step 1255 in which koff is set to 0 if cost2>cost1 and set to 1 if cost2<cost1. Thereafter the run finishes and the process 1160 is directed to the step 1280 to join segments with low cost, described hereinafter in more detail with reference to an example depicted in FIG. 14. Returning to the step 1250, if e2 is not 'mod', the process 1160 follows a NO arrow to a step 1260 which sets the new e1 to be the current e2 and the relevant point after the current e2 becomes the new e2. A following step 1270 determines if the end of the relevant point list has been reached and if not the process follows a NO arrow and goes back to the step 1220. If the step 1270 returns a logical TRUE, the process 1160 follows a YES arrow to the step 1280.

Figure 14:
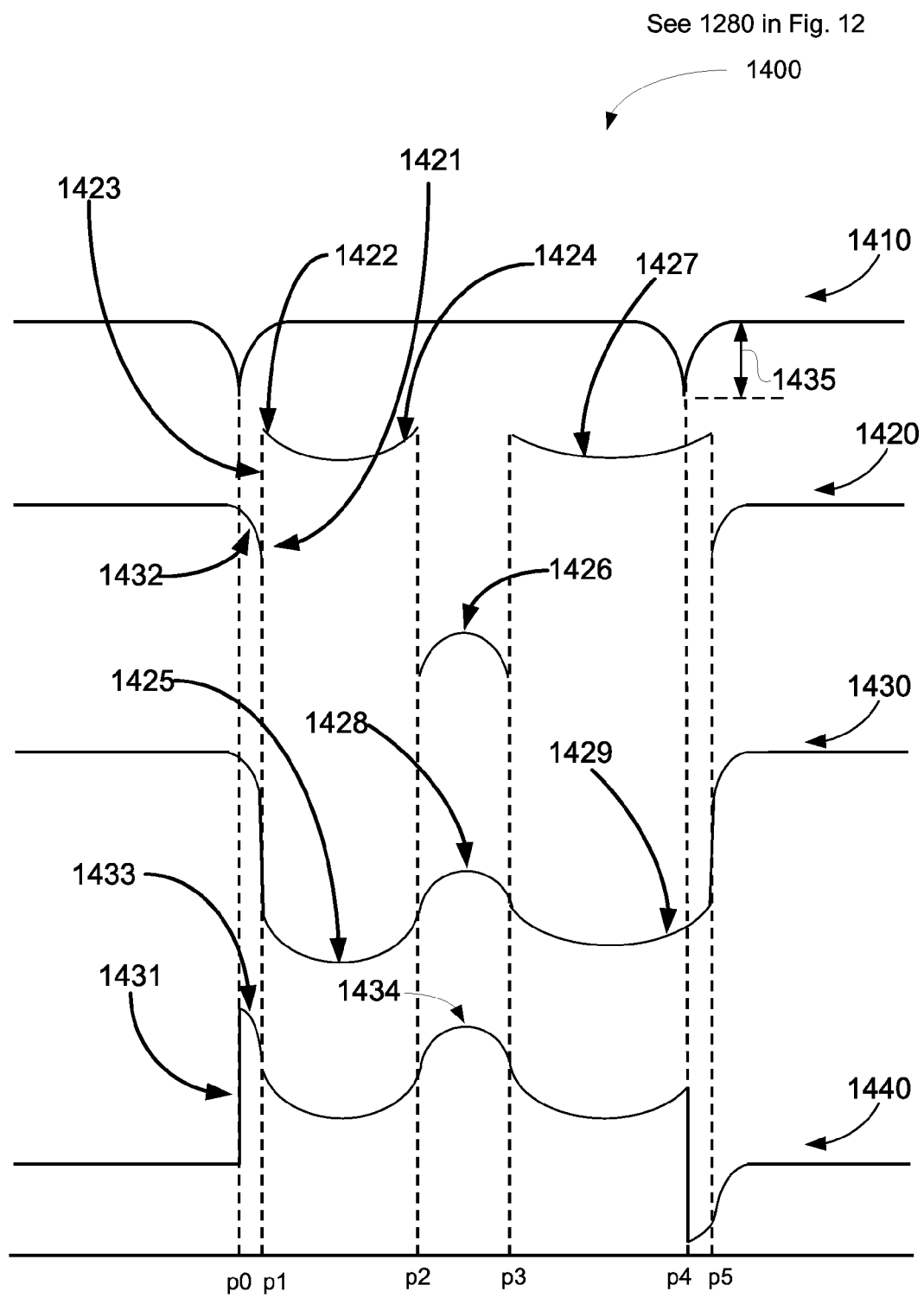
FIG. 14 shows a hypothetical example illustrating a low cost method of joining phase signal segments as used in FIG. 12 according to one MGPU arrangement.

FIG. 14 shows a hypothetical example 1400 illustrating a low cost method of joining phase signal segments as used in FIG. 12 according to one MGPU arrangement. FIG. 14 depicts the entire modulation guided phase unwrapping process (ie the step 520 or the step 620) with a hypothetical example. Through this hypothetical example, the 'joining' step 1280 in FIG. 12 will be explained in detail. In FIG. 14, a reference numeral 1410 represents modulation values for a current scan line in the modulation image $m_x$. There are two modulation minima in 1410 at locations p0 and p4. A reference numeral 1420 depicts wrapped phase values for the current scan line in the phase image $\xi_x$ with 4 discontinuities at locations p1, p2, p3 and p5.

A reference numeral 1430 shows an example of phase unwrapping results without using the modulation image as a guide according to the disclosed MGPU arrangements. At the location p1, because a slope of the phase signal 1420 seems to be consistent before 1421 and after 1422 the discontinuity 1423, current phase unwrapping methods join the signal at p1 by shifting the right hand side signal 1424, ie the segment between p1 and p2, down by $2\pi$ as depicted at 1425. Because of this initial $2\pi$ offset, the unwrapped phase between p2 and p3 ie 1426 and between p3 and p4 ie 1427 are also off by $2\pi$ as depicted by 1428 and 1429 respectively. A reference numeral 1440 shows the correct phase unwrapping result, which are achieved with guidance from the modulation image 1410 according to the disclosed MGPU arrangement.

Referring back to FIG. 12, at the beginning of the process at the step 1210, koff is set to zero and cost1 is set to the distance between p0 and p1, denoted with dist(p0,p1). In the step 1220, p2 is selected as e2. Assuming that the distance between p0 and p5 is smaller than the threshold in the step 1230, since e2 ('neg') is not equal to e1 ('pos') in the example 1440, the process goes to the step 1240 to update the cost1 and cost2. Because the number of relevant points between e0 and e2 is odd at this stage, cost1 is still dist(p0,p1) and cost2 becomes dist(p1,p2). Next in the step 1250, e2 is checked. Since e2 ('neg') at this stage is not 'mod', a new e1 is chosen to be the current e2. Since the end of the relevant point list has not been reached, as determined by the step 1270, a new e2 is chosen by the step 1220 to be p3. Now e1='neg' and e2='pos'. cost1 is updated to be dist(p0,p1)+dist(p2,p3) in the step 1240 and cost2 remains dist(p1,p2). Since e2 is not 'mod', as determined by the step 1250, the process moves to the next iteration, starting with the step 1220. Now e2 is set to p4 and cost2 is updated to be dist(p1,p2)+dist(p3,p4) while cost1 remains dist(p0,p1)+dist(p2,p3). Because e2 is 'mod' this time, koff is updated to 0, assuming cost2=dist(p1,p2)+dist(p3,p4) is greater than cost1=dist(p0,p1)+dist(p2,p3). After koff is updated in the step 1255, the process goes to the step 1280 to 'join segments with low cost'.

For the example in FIG. 14, the step 1280 can choose to join the segments in two different ways, namely (1) treat the discontinuities at p1, p2 and p3 as merely a phase wrapping effect and unwrap accordingly, or (2) treat the discontinuity at p1 as a real phase edge arising from a discontinuity in the object 102, and the discontinuities at p2, p3 as merely phase wrapping effects. The assumption of the cost-efficient unwrapping at the step 1160 is that discontinuities caused merely by phase wrapping effects tend to cut the signal into a series of short segments, while discontinuities caused by real phase edges tend to form much longer segments. In the example of FIG. 14, therefore, phase unwrapping should not occur at p1 because p1 is considered too close to a modulation minimum p0. Accordingly, dist(p0,p1) is small, and therefore the discontinuity at p1 is considered not to be caused by mere phase wrapping, but rather to be caused by a real edge in the phase image. In contrast, the discontinuities at p2 and p3 should be considered to arise merely from phase wrapping because the segment between p2 and p3 is short and there is no modulation minimum nearby. Since cost2=dist(p1,p2)+dist(p3,p4)>cost1=dist(p0,p1)+dist(p2,p3), the above assumption dictates that phase unwrapping should be applied to the segment between p2 and p3, but not to the discontinuity at p1. For position p1, what needs to be done is to replace the location p1 of the discontinuity depicted at 1423 with the real phase edge location p0 as depicted by 1431. The 'join segments with low cost' process step 1280 makes the following phase unwrapping choices. Firstly, that locations p0 and p1 are joined by shifting the segment 1432 between p0 and p1 up, as depicted by 1433. Secondly that p2 and p3 be joined by shifting the segment 1426 between p2 and p3 up, as depicted by 1434. The alternative choice of joining p1 and p2 (ie shifting the segment 1424 between p1 and p2 down) and joining p3 and p4 (ie shifting the segment 1427 between p3 and p4 down) not only gives the incorrect result in 1430, but also operates on a longer signal, given cost2=dist(p1,p2)+dist(p3,p4) >cost1=dist(p0,p1)+dist(p2,p3), thus considered 'high cost'.

The main difference between the step 1280 and the 'join e0 and e1' process (ie the step 1145 and the step 1155) is that the step 1280 is only handling cases where the first relevant point e0 is 'mod' followed by a 'pos' or 'neg' relevant point, while the step 1145 only handles cases where e1 is 'mod' and e0 is 'pos' or 'neg'. The step 1155 only handles cases where e0 and e1 are 'opposite' (one of them is 'pos' and the other one 'neg').

MGPU Arrangement No. 2

This MGPU arrangement performs all the steps in the first MGPU arrangement with a slightly different joining step performed by the step 1145, 1155 and 1280. In real phase imaging situations, it is possible for a phase edge to be more than 2π. In other words, while it is important to distinguish between real phase edges and simple phase wrapping effect, it is possible for the real phase edge to be a wrapped phase edge.

Figure 15:
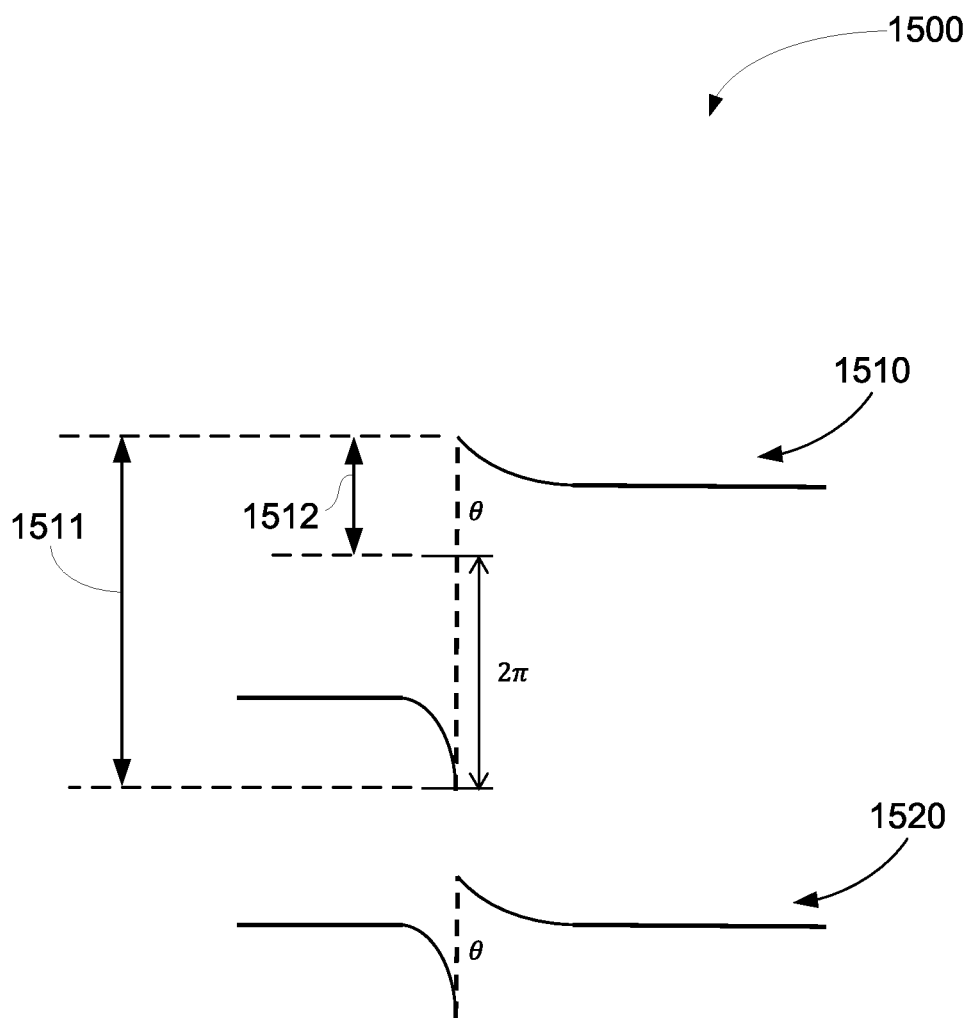
FIG. 15 illustrates an example of wrapped phase edge according to one MGPU arrangement.

FIG. 15 illustrates a hypothetical example 1500 of wrapped phase edge according to the second MGPU arrangement. In 1510, a phase edge 1511 of size (2π+θ) will appear to be a phase edge 1512 of size θ as depicted at 1520, in the wrapped phase image. This phase wrapping effect will not be detected with information of modulation minimum location alone. In order to tell the difference between 1510 and 1520, more information is needed.

It has been observed that the modulation minimum in the modulation image not only gives the real location of the phase edge, but the amplitude of the modulation minimum also has a near-linear relationship with the underlying phase edge size within a certain range S, as described in more detail with reference to FIG. 19. That is, when a phase edge size 1511 is less than a certain value, 3π for example, a magnitude 1435 of a modulation reduction (ie the difference between the value of the modulation minimum and its surroundings) at the modulation minimum location is a monotonically increasing function of the underlying phase edge size. For a specific XTI system set-up, it is possible to measure the modulation drop values with an artificial phase object that has a known phase jump within said certain range S, and to use the measured modulation drop values as a reference (referred to as a modulation drop reference value). For example, a plastic ball with known diameter and refractive index can be used to calibrate the phase jump. Using these measured modulation drop reference values, it is possible to estimate if a real phase edge is wrapped (reduced) by 2π or more due to phase wrapping effect. For example, if the real phase edge in the x direction is 7π/2, the demodulated phase image $\xi_x(r)$ will be 3π/2 due to phase wrapping effect. If, however, the modulation drop close to the discontinuity is greater than the modulation drop reference value obtained using an artificial phase object with 3π phase jump, it is possible to infer that the real phase edge is 3π/2 plus 2π ie 7π/2. It is also possible to use several reference phase objects with phase edges at different sizes so that a range of phase jump values can be recovered.

That is, in the steps 1145, 1155 and 1280, when joining phase signals at discontinuities, the modulation drop value and the associate modulation drop reference values need to be considered.

The modulation drop values can also be used to check the accuracy of the phase unwrapping results. As the modulation drop values are assumed to be proportional to the underlying phase edge size, a small phase edge should have a small modulation drop and a large edge should have a correspondingly large modulation drop. If a phase edge is incorrectly estimated for example due to propagated error from a previous phase unwrapping point, the modulation drop associated with this particular phase edge can be compared with modulation drop associated with other edges to determine if there is an inconsistency.

Figure 19:
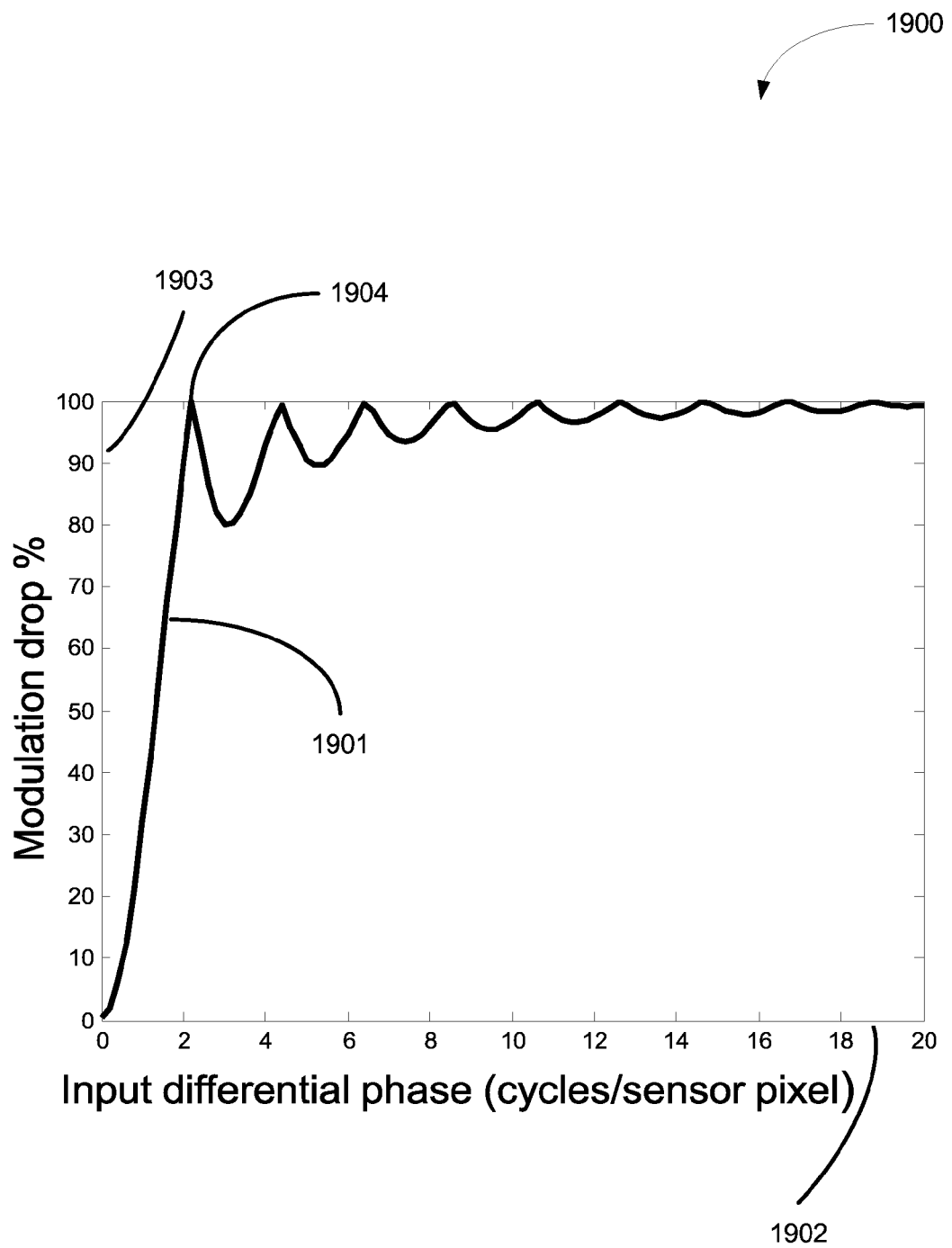
FIG. 19 depicts the linear relationship which exists between phase size and modulation drop 1903 for phase values less than a particular phase threshold.

FIG. 19 shows an example 1900 of a linear relationship 1901 between phase size 1902 and modulation drop 1903 for phase values less than a particular phase threshold 1904.

INDUSTRIAL APPLICABILITY

The arrangements described are applicable to the computer and data processing industries and particularly for the X-ray imaging industry.

The foregoing describes only some embodiments of the present invention, and modifications and/or changes can be made thereto without departing from the scope and spirit of the invention, the embodiments being illustrative and not restrictive.

We claim:

1. A method for determining a phase for a captured image, the method comprising the steps of:
    forming a demodulated image from the captured image, said demodulated image defining a plurality of wrapped phase values and a plurality of modulation values, each wrapped phase value and each modulation value being associated with at least one region in the captured image;
    identifying a position of an edge in the captured image dependent upon the plurality of modulation values;
    determining a position of substantial change in the wrapped phase values in the captured image dependent upon the identified position of the edge, and;
    determining at least one unwrapped phase value based on the position of the edge and the position of the substantial change in the wrapped phase values by shifting a position of the substantial change in the wrapped phase values to the identified position of the edge, so that said unwrapped phase value is adjusted by at least one cycle.

2. A method according to claim 1, wherein the step of identifying the position of the edge in the captured image comprises comparing neighbouring modulation values along a scan line of the modulation values to identify a local minimum in the modulation values.

3. A method according to claim 2, wherein the step of shifting the position of the substantial change in the wrapped phase values comprises shifting phase values for pixels between the position of substantial change in the wrapped phase values and the identified local minimum in the plurality of modulation values by at least one cycle.

4. A method according to claim 2, wherein the step of shifting the position of the substantial change in the wrapped phase values comprises the steps of:
    determining a magnitude of a reduction in a modulation value at the local minimum; and
    shifting the position of the substantial change in the wrapped phase values by at least one cycle dependent upon said determined magnitude.

5. A method according to claim 1, wherein the step of determining a position of substantial change in the wrapped phase values comprises determining phase differences along a scan line of the wrapped phase values to identify a discontinuity in the wrapped phase values.

6. A method according to claim 1, wherein the step of shifting the position of the substantial change in the wrapped phase values comprises the steps of:
    comparing neighbouring modulation values along a scan line of the modulation values to identify a local minimum in the modulation values;
    determining phase differences along a scan line of the wrapped phase values to identify a discontinuity in the wrapped phase values; and
    shifting the identified discontinuity to the position of the local minimum.

7. A method determining a phase for a captured image, the method comprising:
  forming a demodulated image from the captured image, said demodulated image defining a plurality of wrapped phase values and a plurality of modulation values, each wrapped phase value and each modulation value being associated with at least one region in the captured image;
  identifying an edge position in the captured image by analysing the plurality of modulation values;
  determining a position of substantial change in the wrapped phase values in the captured image dependent upon the identified edge position;
  determining at least one unwrapped phase value by shifting the position of substantial change in the wrapped phase values to the identified edge position, so that said phase value is adjusted by at least one cycle.

8. A method determining a phase for a captured image, the method comprising:
  forming a demodulated image from the captured image, said demodulated image defining a plurality of wrapped phase values and a plurality of modulation values, each wrapped phase value and each modulation value being associated with at least one region in the captured image;
  determining an unwrapped phase for the region of the captured image by refining a position of substantial change in the wrapped phase values using the modulation values, wherein the unwrapped phase value at the refined position is determined by adjusting at least one wrapped phase value in the vicinity of the refined position to at least one cycle.

9. A phase unwrapping method, the method comprising:
  demodulating a captured image to determine a plurality of wrapped phase values and a plurality of modulation values, each wrapped phase value and each modulation value being associated with a region in the captured image; and
  unwrapping a phase for said region of the captured image using the wrapped phase values and a position of a local minimum in the modulation values,
  wherein unwrapping the phase for said region further comprises adjusting the wrapped phase values based on the position of the local minimum in the modulation values,
  wherein the wrapped phase values are adjusted in the vicinity of the position of substantial change in the wrapped phase values,
  wherein the wrapped phase values are adjusted by at least one cycle to shift a position of substantial change in the wrapped phase values to the position of the local minimum in the modulation values.

10. An apparatus for determining a phase for a captured image, the apparatus comprising:
  a processor; and
  a memory storing a computer executable program for directing the processor to perform a method comprising the steps of:
    forming a demodulated image from the captured image, said demodulated image defining a plurality of wrapped phase values and a plurality of modulation values, each wrapped phase value and each modulation value being associated with at least one region in the captured image;
    identifying a position of an edge in the captured image dependent upon the plurality of modulation values;
    determining a position of substantial change in the wrapped phase values in the captured image dependent upon the identified position of the edge, and;
    determining at least one unwrapped phase value based on the position of the edge and the position of the substantial change in the wrapped phase values by shifting a position of the substantial change in the wrapped phase values to the identified position of the edge, so that said unwrapped phase value is adjusted by at least one cycle.

11. A non-transitory computer readable storage medium storing a computer executable program for directing a processor to perform a method for determining a phase for a captured image, the method comprising the steps of:
  forming a demodulated image from the captured image, said demodulated image defining a plurality of wrapped phase values and a plurality of modulation values, each wrapped phase value and each modulation value being associated with at least one region in the captured image;
  identifying a position of an edge in the captured image dependent upon the plurality of modulation values;
  determining a position of substantial change in the wrapped phase values in the captured image dependent upon the identified position of the edge, and;
  determining at least one unwrapped phase value based on the position of the edge and the position of the substantial change in the wrapped phase values by shifting a position of the substantial change in the wrapped phase values to the identified position of the edge, so that said unwrapped phase value is adjusted by at least one cycle.

12. An unwrapped phase record determined from wrapped phase values and a plurality of modulation values from a captured image, the unwrapped phase record being determined using a method comprising the steps of:
  forming a demodulated image from the captured image, said demodulated image defining the plurality of wrapped phase values and the plurality of modulation values, each wrapped phase value and each modulation value being associated with at least one region in the captured image;
  identifying a position of an edge in the captured image dependent upon the plurality of modulation values;
  determining a position of substantial change in the wrapped phase values in the captured image dependent upon the identified position of the edge, and;
  determining at least one unwrapped phase value in the unwrapped phase record based on the position of the edge and the position of the substantial change in the wrapped phase values by shifting a position of the substantial change in the wrapped phase values to the identified position of the edge, so that said unwrapped phase value is adjusted by at least one cycle.

* * * * *